United States Patent [19]

Angerbauer et al.

[11] Patent Number: 4,988,711

[45] Date of Patent: Jan. 29, 1991

[54] HMG-COA REDUCTARE-INHIBITING N-SUBSTITUTED N-AMINO-PYRROLES

[75] Inventors: Rolf Angerbauer; Walter Hübsch; Peter Fey; Hilmar Bischoff, all of Wuppertal; Dieter Petzinna, Duesseldorf; Delf Schmidt, Wuppertal, all of Fed. Rep. of Germany; Günter Thomas, Arese, Italy

[73] Assignee: Bayer Aktiengesellschaft, Leverkusen, Fed. Rep. of Germany

[21] Appl. No.: 337,001

[22] Filed: Apr. 12, 1989

[30] Foreign Application Priority Data

Apr. 23, 1988 [DE] Fed. Rep. of Germany ....... 3813776
Oct. 11, 1988 [IT] Italy ................. 22264 A/88

[51] Int. Cl.$^5$ .................. A61K 31/445; C07D 401/04
[52] U.S. Cl. .................. 514/326; 514/212; 514/422; 514/426; 540/480; 546/208; 546/207; 546/277; 546/143; 546/144; 546/159; 546/167; 548/518; 548/517; 548/557; 548/162; 548/212; 548/233; 548/245; 548/167; 548/471; 548/453; 548/217; 548/305; 544/333; 544/336; 544/238; 544/237; 544/284; 544/353; 544/235
[58] Field of Search ............. 540/480; 546/208, 207; 548/518, 517, 557; 514/326, 422, 426, 212

[56] References Cited

FOREIGN PATENT DOCUMENTS 0221025 5/1987 European Pat. Off. ............ 548/518

Primary Examiner—Robert T. Bond

Attorney, Agent, or Firm—Sprung Horn Kramer & Woods

[57] ABSTRACT

Inhibiting HMG-CoA reductase, as in treating hyperlipopproteinaemia, lipoproteinaemia and arteriosclerosis, with the new N-substituted N-amino-pyrroles of the formula

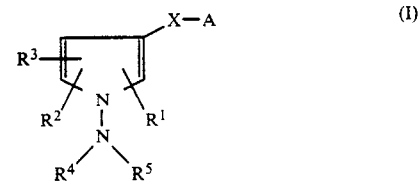

in which
$R^1$ is an organic radical,
$R^2$ is an aryl or heteroaryl radical,
$R^3$ is a hydrogen or an organic radical,
$R^4$ and $R^5$ each independently is hydrogen or an organic radical or, together, they complete a heterocylic ring,
X is —CH$_2$—CH$_2$— or —CH=CH—,
A is

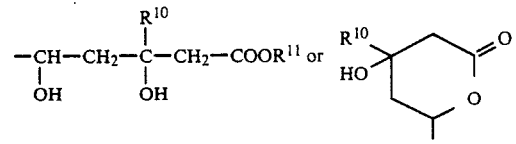

$R^{10}$ is hydrogen or alkyl, and
$R^{11}$ is hydrogen, an organic radical or a cation.

11 Claims, No Drawings

HMG-COA REDUCTARE-INHIBITING N-SUBSTITUTED N-AMINO-PYRROLES

The invention relates to substituted pyrroles, intermediates for their preparation, their preparation and their use in medicaments.

It has been disclosed that certain indole derivatives or pyrazole derivatives are inhibitors of 3-hydroxy-3-methyl-glutaryl coenzyme A reductase (HMG-CoA reductase) [EP-A 1,114,027; U.S. Pat. No. 4,613,610].

Substituted pyrroles of the general formula (I)

$$\begin{array}{cc}
R^2 \diagdown \quad X{-}A \quad R^1 & R^1 \diagdown \quad X{-}A \\
\big\| & \big\| \\
R^3 {-} N {-} R^1 & R^3 {-} N {-} R^2 \\
\quad \big| & \quad \big| \\
\quad N & \quad N \\
R^4 \diagup \diagdown R^5 & R^4 \diagup \diagdown R^5 \\
\text{(Ia)} & \text{(Ib)}
\end{array}$$

in which $R^1$ stands for cycloalkyl, or
stands for alkyl which can be substituted by halogen, cyano, hydroxyl, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^6R^7$, wherein
$R^6$ and $R^7$ are identical or different and denote alkyl, aryl, aralkyl, acyl, alkylsulphonyl or arylsulphonyl,
or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the last-mentioned substituents can be monosubstituted, disubstituted or trisubstituted by identical or different halogen, cyano, trifluoromethyl, trifluoromethoxy, alkyl, alkoxy, alkylthio or alkylsulphonyl, $R^2$ stands for heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^6R^7$, wherein
$R^6$ and $R^7$ have the abovementioned meanings, or
stands for aryl which can be monosubstituted to pentasubstituted by identical or different alkyl, hydroxyalkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^6R^7$, 60 wherein
$R^6$ and $R^7$ have the abovementioned meanings, $R^3$ stands for hydrogen, or
stands for cycloalkyl, or
stands for alkyl which can be substituted by halogen, cyano, hydroxyl, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^6R^7$, wherein
$R^6$ and $R^7$ have the abovementioned meanings,
or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the lastmentioned substituents can be monosubstituted, disubstituted or trisubstituted by identical or different halogen, cyano, trifluoromethyl, trifluoromethoxy, alkyl, alkoxy, alkylthio or alkylsulphonyl, or
stands for heteroaryl which can be monosubstituted, disubstituted or trisubstituted by identical or different halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^6R^7$, wherein
$R^6$ and $R^7$ have the abovementioned meanings, or
stands for aryl which can be monosubstituted to pentasubstituted by identical or different alkyl, hydroxyalkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^6R^7$, wherein
$R^6$ and $R^7$ have the abovementioned meanings, $R^4$ and $R^5$ are identical or different and stand for hydrogen,
stand for cycloalkyl, or
stand for alkyl which can be substituted by halogen, hydroxyl, alkoxy, alkylthio or acyl, or by a group of the formula —$NR^6R^7$, wherein
$R^6$ and $R^7$ have the abovementioned meanings,
or by carbamoyl, heteroaryl, aryl, aryloxy or arylthio, where the heteroaryl and aryl radicals of the last-mentioned substituents can be monosubstituted, disubstituted or trisubstituted by identical or different halogen, trifluoromethyl, alkyl, alkoxy, alkylthio or alkylsulphonyl, or
stand for heteroaryl which can be monosubstituted or disubstituted by identical or different halogen, alkyl, alkoxy, alkylthio, alkylsulphonyl, aryl, trifluoromethyl or alkoxycarbonyl, or by a group of the formula —$NR^6R^7$, wherein
$R^6$ and $R^7$ have the abovementioned meanings, or
stand for aryl which can be monosubstituted or disubstituted by identical or different alkyl, hydroxyalkyl, alkoxy, alkylthio, alkylsulphonyl, halogen, cyano, nitro, trifluoromethyl, alkoxycarbonyl or carbamoyl, or by a group of the formula —$NR^6R^7$, wherein
$R^6$ and $R^7$ have the abovementioned meanings, or
$R^4$ and $R^5$, together with the N atom, form a 4- to 8-membered heterocycle which can contain a further heteroatom Y, where
Y stands for S, O or N—$R^8$, where
$R^8$ denotes alkyl, aryl, aralkyl, acyl, alkylsulphonyl or arylsulphonyl,
where this heterocycle can be substituted by $R^9$, where R⁹ stands for cycloalkyl, or
stands for alkyl which can be substituted by halogen, hydroxyl, alkoxy, alkylthio or acyl, or by a group of the formula —NR⁶R⁷, wherein
R⁶ and R⁷ have the abovementioned meanings, or by carbamoyl, heteroaryl, aryl, aryloxy or arylthio, where the heteroaryl and aryl radicals of the last-mentioned substituents can be monosubstituted or disubstituted by identical or different halogen, trifluoromethyl, alkyl, alkoxy, alkylthio or alkylsulphonyl,
or
stands for heteroaryl which can be monosubstituted or disubstituted by identical or different halogen, alkyl, alkoxy, alkylthio, alkylsulphonyl, aryl, trifluoromethyl or alkoxycarbonyl, or by a group of the formula —NR⁶R⁷, wherein
R⁶ and R⁷ have the abovementioned meanings,
or
stands for aryl which can be monosubstituted or disubstituted by identical or different alkyl, hydroxyalkyl, alkoxy, alkylthio, alkylsulphonyl, halogen, cyano, nitro, trifluoromethyl, alkoxycarbonyl or carbamoyl, or by a group of the formula —NR⁶R⁷, wherein
R⁶ and R⁷ have the abovementioned meanings,
X stands for a group of the formula —CH₂—CH₂— or —CH=CH—, and
A stands for a group of the formula

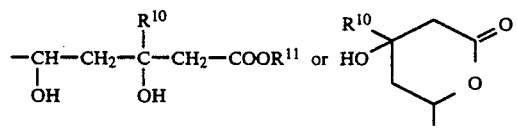

where
R¹⁰ denotes hydrogen or alkyl and
R¹¹ denotes hydrogen,
an alkyl, aryl or aralkyl radical, or
a cation.

Surprisingly, the substituted pyrroles according to the invention show a good inhibitory action on HMG-CoA reductase (3-hydroxy-3-methyl-glutaryl coenzyme A reductase).

Cycloalkyl in general stands for a cyclic hydrocarbon radical having 3 to 8 carbon atoms. The cyclopropyl, cyclopentyl and cyclohexyl ring is preferred. Examples which may be mentioned are cyclopropyl, cyclopentyl, cyclohexyl, cycloheptyl and cyclooctyl.

Alkyl in general stands for a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy and isooctoxy.

Alkylthio in general stands for a straight-chain or branched hydrocarbon radical having 1 to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio and isooctylthio.

Alkylsulphonyl in general stands for a straight-chain or branched hydrocarbon radical having 1 to 12 carbon atoms which is bonded via an SO₂ group. Lower alkylsulphonyl having 1 to about 6 carbon atoms is preferred. Examples which may be mentioned are methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

Aryl in general stands for an aromatic radical having 6 to about 12 carbon atoms. Preferred aryl radicals are phenyl, naphthyl and biphenyl.

Aryloxy in general stands for an aromatic radical having 6 to about 12 carbon atoms which is bonded via an oxygen atom. Preferred aryloxy radicals are phenoxy and naphthyloxy.

Arylthio in general stands for an aromatic radical having 6 to about 12 carbon atoms which is bonded via a sulphur atom. Preferred arylthio radicals are phenylthio and naphthylthio.

Arylsulphonyl in general stands for an aromatic radical having 6 to about 12 carbon atoms which is bonded via an SO₂ group. Examples which may be mentioned are phenylsulphonyl, naphthylsulphonyl and biphenylsulphonyl. Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy.

Aralkylthio in general stands for an aralkyl radical having 7 to about 14 carbon atoms, the alkyl chain being bonded via a sulphur atom. Aralkylthio radicals having 1 to 6 carbon atoms in the aliphatic moiety and 6 to 12 carbon atoms in the aromatic moiety are preferred. Examples which may be mentioned are the following aralkylthio radicals: benzylthio, naphthylmethylthio, phenethylthio and phenylpropylthio.

Aralkylsulphonyl in general stands for an aralkyl radical having 7 to about 14 carbon atoms, the alkyl radicals being bonded via an SO₂ link. Aralkylsulphonyl radicals having 1 to 6 carbon atoms in the aliphatic moiety and 6 to 12 carbon atoms in the aromatic moiety are preferred. Examples which may be mentioned are the following aralkylsulphonyl radicals: benzylsulphonyl, naphthylmethylsulphonyl, phenethylsulphonyl and phenylpropylsulphonyl.

Alkoxycarbonyl can be represented, for example, by the formula

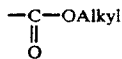

In this connection, alkyl stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl and isobutoxycarbonyl.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are benzoyl, acetyl, ethylcarbonyl, propylcarbonyl, isopropylcarbonyl, butylcarbonyl and isobutylcarbonyl.

Halogen in general stands for fluorine, chlorine, bromine or iodine, preferably for fluorine, chlorine or bromine. Particularly preferably, halogen stands for fluorine or chlorine.

Heteroaryl in the context of the abovementioned definition in general stands for a 5- to 6-membered aromatic ring which can contain oxygen, sulphur and/or nitrogen as heteroatoms and onto which can be fused further aromatic rings. 5- and 6-membered aromatic rings which contain one oxygen, one sulphur and/or up to 2 nitrogen atoms and which are optionally fused to benzene are preferred. Heteroaryl radicals which may be mentioned as particularly preferred are thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolinyl, thiazolyl, benzothiazolyl, isothiazolyl, oxazolyl, benzoxazolyl, isoxazolyl, imidazolyl, benzimidazolyl, pyrazolyl, indolyl and isoindolyl.

Sulphamoyl (aminosulphonyl) stands for the group $SO_2-NH_2$.

If $R^{11}$ stands for alkyl, aryl or aralkyl, it forms an ester. In the context of the present invention, physiologically tolerable esters which are easily hydrolyzed in vivo to give a free carboxyl group and a corresponding physiologically tolerable alcohol are preferred. These preferably include alkyl esters ($C_1$ to $C_4$) and aralkyl esters ($C_7$ to $C_{10}$), preferably lower alkyl esters and benzyl esters. Moreover, the following ester radicals may be mentioned: methyl esters, ethyl esters, propyl esters and benzyl esters.

If $R^{11}$ stands for a cation, a physiologically tolerable metal cation or ammonium cation is preferably meant. In this connection, alkali metal cations or alkaline earth metal cations such as, for example, sodium cations, potassium cations, magnesium cations or calcium cations, and aluminum cations or ammonium cations, and nontoxic substituted ammonium cations from amines such as dilower alkylamines, trilower alkylamines, dibenzylamine, N,N'-dibenzylethylenediamine, N-benzyl-8-phenylethylamine, N-methylmorpholine or N-ethylmorpholine, dihydroabietylamine, N,N'-bis-dihydroabietylethylenediamine, N-lower alkylpiperidine and other amines which can be used for the formation of salts are preferred.

In the context of the present invention, the N-substituted N-amino-pyrroles (I) correspond to the general formula

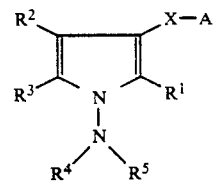

and

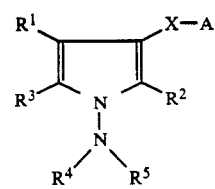

where
$R^1$, $R^2$, $R^3$, $R^4$, $R^5$, X and A have the abovementioned meanings.

In the context of the general formula (I), compounds having the general formulae (Ia) and (Ib) are preferred.

Preferred compounds of the general formula (I) are those in which
$R^1$ stands for cyclopropyl, cyclopentyl or cyclohexyl, or
  stands for lower alkyl which can be substituted by fluorine, chlorine, bromine, cyano, hydroxyl, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, by a group of the formula $-NR^6R^7$, wherein
    $R^6$ and $R^7$ are identical or different and denote lower alkyl, phenyl, benzyl, acetyl, benzoyl, phenylsulphonyl or lower alkylsulphonyl,
  or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by identical or different fluorine, chlorine, bromine, lower alkyl, lower alkoxy, trifluoromethyl or trifluoromethoxy,
$R^2$ stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl, or
  stands for phenyl or naphthyl, each of which can be monosubstituted to tetrasubstituted by identical or different lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —NR$^6$R$^7$, where R$^6$ and R$^7$ have the abovementioned meanings, R$^3$ - stands for hydrogen or for cyclopropyl, cyclopentyl or cyclohexyl or or for lower alkyl which can be substituted by fluorine, chlorine, cyano, hydroxyl, lower alkoxy, lower alkylthio, lower alkylsulphonyl, trifluoromethyl, lower alkoxycarbonyl, benzoyl or lower alkylcarbonyl, or by a group of the formula —NR$^6$R$^7$, wherein R$^6$ and R$^7$ have the abovementioned meanings, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylsulphonyl, benzyloxy or phenylethoxy, where the heteroaryl and aryl radicals mentioned can be monosubstituted or disubstituted by identical or different fluorine, chlorine, lower alkyl, lower alkoxy or trifluoromethyl, stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, which can be monosubstituted or disubstituted by identical or different fluorine, chlorine, lower alkyl, lower alkoxy, phenyl, phenoxy, trifluoromethyl or lower alkoxycarbonyl, or denotes phenyl or naphthyl, which can be monosubstituted or disubstituted by identical or different lower alkyl, lower hydroxyalkyl, lower alkoxy, phenyl, phenyloxy, benzyl, benzyloxy, phenethyl, phenylethoxy, fluorine, chlorine, cyano, trifluoromethyl or lower alkoxycarbonyl, or by a group of the formula —NR$^6$R$^7$, where R$^6$ and R$^7$ have the abovementioned meanings, R$^4$ and R$^5$ can be identical or different and stand for hydrogen, stand for cyclopropyl, cyclopentyl or cyclohexyl or stand for lower alkyl which can be substituted by fluorine, chlorine, hydroxyl, lower alkoxy, trifluoromethyl or benzoyl, or by a group of the formula —NR$^6$R$^7$, wherein R$^6$ and R$^7$ have the abovementioned meanings, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, benzyloxy oxy or phenylethoxy, where the heteroaryl and aryl radicals mentioned can be monosubstituted or disubstituted by identical or different fluorine, chlorine, lower alkyl, lower alkoxy or trifluoromethyl, stand for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, lower alkyl, lower alkoxy, phenyl, phenoxy, trifluoromethyl or lower alkoxycarbonyl, or stand for phenyl or naphthyl, each of which can be monosubstituted or disubstituted by identical or different lower alkyl, lower alkoxy, lower alkylthio, lower alkylsulphonyl, phenyl, phenyloxy, phenylthio, phenylsulphonyl, benzyl, benzyloxy, phenethyl, phenylethoxy, fluorine, chlorine, cyano, trifluoromethyl or lower alkoxycarbonyl, or by a group of the formula —NR$^6$R$^7$, where R$^6$ and R$^7$ have the abovementioned meanings, or R$^4$ and R$^5$, together with the N atom, form a 5- to 7-membered heterocycle which can contain a further heteroatom Y where Y stands for S, O or N—R$^8$, where R$^8$ stands for lower alkyl, phenyl, benzyl, lower alkylsulphonyl, phenylsulphonyl, benzoyl, or acetyl, where this heterocycle can be substituted by R$^9$, where R$^9$ stands for cyclopropyl, cyclopentyl or cyclohexyl or stands for lower alkyl which can be substituted by fluorine, chlorine, hydroxyl, lower alkoxy, benzoyl or lower alkylcarbonyl, wherein R$^6$ and R$^7$ have the abovementioned meanings, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylsulphonyl, benzyloxy or phenylethoxy, where the heteroaryl and aryl radicals mentioned can be monosubstituted or disubstituted by identical or different fluorine, chlorine, hydroxyalkyl, lower alkyl, lower alkoxy or trifluoromethyl, stands for thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, lower alkyl, lower alkoxy, phenyl, phenoxy, trifluoromethyl or lower alkoxycarbonyl, or stands for phenyl which can be monosubstituted or disubstituted by identical or different lower alkyl, lower alkoxy, lower alkylsulphonyl, phenyl, phenyloxy, phenylsulphonyl, benzyl, benzyloxy, phenethyl, phenylethoxy, fluorine, chlorine, cyano, trifluoromethyl or lower alkoxycarbonyl, or by a group of the formula —NR$^6$R$^7$, where R$^6$ and R$^7$ have the abovementioned meanings, X stands for a group of the formula —CH$_2$—CH$_2$— or —CH=CH—, A stands for a group of the formula

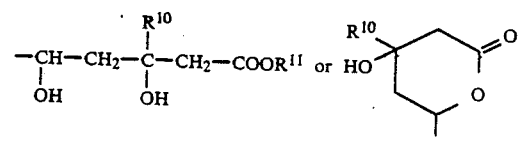

wherein

R$^{10}$ denotes hydrogen or lower alkyl, and

R$^{11}$ denotes a C$_1$–C$_6$-alkyl radical, a C$_6$–C$_{12}$-alkyl radical or a C$_7$–C$_{10}$-alkyl radical or denotes a physiologically tolerable cation.

Compounds of the general formulae (Ia) and (Ib) are particularly preferred in which R$^1$ stands for cyclopropyl, cyclopentyl or cyclohexyl, or stands for methyl, ethyl, propyl, isopropyl, butyl, sec.-butyl or tert.butyl, each of which can be substituted by fluorine, chlorine, hydroxyl, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylsulphonyl, benzyloxy, benzylthio or benzylsulphonyl, $R^2$ stands for pyridyl, pyrimidyl, quinolyl or isoquinolyl, each of which can be substituted by fluorine, chlorine, methyl, methoxy or trifluoromethyl or stands for phenyl which can be monosubstituted or disubstituted by identical or different methyl, ethyl, propyl, isopropyl, butyl, isobutyl, tert.-butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, methoxycarbonyl, ethoxycarbonyl, propoxycarbonyl, isopropoxycarbonyl, butoxycarbonyl, isobutoxycarbonyl or tert.-butoxycarbonyl, $R^3$ denotes hydrogen, cyclopropyl, cyclopentyl or cyclohexyl or denotes methyl, ethyl, propyl, isopropyl, butyl, isobutyl, tert.butyl, pentyl, isopentyl, hexyl or isohexyl, which can be substituted by fluorine, chlorine, cyano, hydroxyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group —$NR^6R^7$, where $R^6$ and $R^7$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, $R^4$ and $R^5$ can be identical or different and stand for hydrogen, cyclopropyl, cyclopentyl or cyclohexyl, or stand for methyl, ethyl, propyl, isopropyl, butyl, isobutyl, tert.butyl, pentyl, isopentyl, hexyl or isohexyl, each of which can be substituted by fluorine, chlorine, hydroxyl, methoxy, ethoxy, methylthio, ethylthio, propylthio, isopropylthio, butylthio, isobutylthio, tert.butylthio, benzoyl, acetyl or ethylcarbonyl, or by a group —$NR^6R^7$, where $R^6$ and $R^7$ have the abovementioned meanings, or by pyrrolyl, pyridyl, pyrimidyl, pyrazinyl, pyridazinyl, quinolyl, isoquinolyl, thienyl, furyl, phenyl, phenoxy, phenylthio, phenylsulphonyl and benzyloxy, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.-butoxy or trifluoromethyl, or stand for thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzothiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or stand for phenyl which can be monosubstituted or disubstituted by identical or different methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, phenyl, phenoxy, phenylthio, phenylsulphonyl, benzyl, benzyloxy, fluorine, chlorine, cyano, hydroxyl, trifluoromethyl, methoxycarbonyl, ethoxycarbonyl, propoxycarbonyl, isopropoxycarbonyl, butoxycarbonyl, isobutoxycarbonyl or tert.butoxycarbonyl, or by a group —$NR^6R^7$, where $R^6$ and $R^7$ have the abovementioned meanings, or $R^4$ and $R^5$, together with the N atom, form a 5- to 7-membered heterocycle which can contain a further heteroatom Y, where Y stands for S, O or N—$R^8$, where $R^8$ can denote methyl, ethyl, propyl, isopropyl, butyl, isobutyl, tert.-butyl, phenyl, benzyl, acetyl, methylsulphonyl, ethylsulphonyl, propylsulphonyl, isopropylsulphonyl or phenylsulphonyl, where this heterocycle can be substituted by $R^9$ where $R^9$ stands for cyclopropyl, cyclopentyl or cyclohexy or stands for methyl, ethyl, propyl, isopropyl, butyl, isobutyl, tert.-butyl, pentyl, isopentyl, hexyl or isohexyl, each of which can be substituted by fluorine, chlorine, hydroxyl, methoxy, ethoxy, trifluoromethyl, benzoyl, butyl or ethylcarbonyl, or by a group —$NR^6R^7$ where $R^6$ and $R^7$ have the abovementioned meanings, stands for pyridyl, pyrimidyl or benzimidazolyl, which can be monosubstituted or disubstituted by identical or different fluorine, chlorine, methyl, ethyl, methoxy, ethoxy, phenyl, phenoxy or trifluoromethyl, stands for phenyl which can be monosubstituted or disubstituted by identical or different methyl, ethyl, propyl, tert.-butyl, methylsulphonyl, ethylsulphonyl, propylsulphonyl, phenyl, phenyloxy, phenylsulphonyl, benzyl, benzyloxy, phenethyl, phenylethoxy, fluorine, chlorine, cyano or trifluoromethyl, or by a group of the formula —$NR^6R^7$, where $R^6$ and $R^7$ have the abovementioned meanings, X stands for a group of the formula —$CH_2$—$CH_2$— or —CH=CH—, A stands for a group of the formula

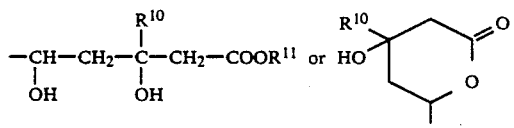

wherein $R^{10}$ denotes hydrogen, methyl, ethyl, propyl, isopropyl, butyl, isobutyl or tert.butyl, and $R^{11}$ denotes hydrogen, methyl, ethyl, propyl, isopropyl, butyl, isobutyl, tert.butyl or benzyl or denotes a sodium, potassium, calcium or magnesium or ammonium ion.

The substituted pyrroles of the general formula (I) according to the invention have several asymmetric carbon atoms and can therefore exist in various stereochemical forms. The invention relates both to the individual isomers and to their mixtures.

Depending on the meaning of the group X or the radical A, different stereoisomers result which are illustrated in more detail in the following:

(a) If the group —X— stands for a group of the formula —CH=CH—, then compounds according to the invention can exist in two stereoisomeric forms which can have the E configuration (II) or Z configuration (III) on the double bond:

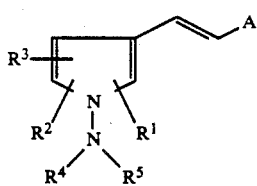

(II) E form

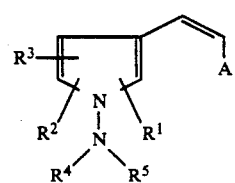

(III) Z form where $R^1$, $R^2$, $R^3$, $R^4$, $R^5$ and A have the abovementioned meanings.

Those compounds of the general formula (I) which have the E configuration (II) are preferred.

(b) If the radical —A— stands for a group of the formula

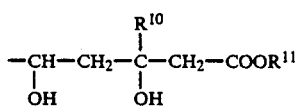

where $R^{10}$ and $R^{11}$ have the abovementioned meanings, then the compounds of the general formula (I) possess at least two asymmetric carbon atoms, namely the two carbon atoms to which the hydroxyl groups are bonded. Depending on the relative position of these hydroxyl groups to one another, the compounds according to the invention can be present in the erythro configuration (IV) or in the threo configuration (V).

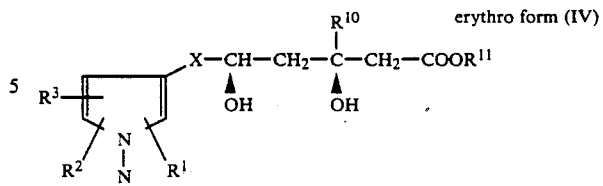

erythro form (IV)

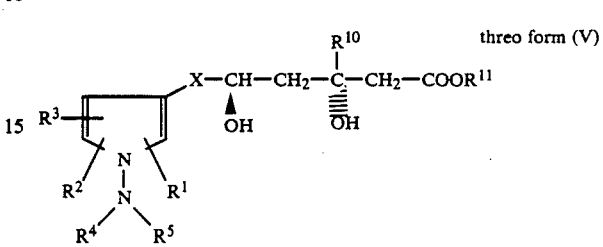

threo form (V)

Two enantiomers exist, in turn, both of the compounds in the erythro and in the threo configuration, namely the 3R,5S-isomer or 3S,5R-isomer (erythro form) and 3R,5R-isomer and 3S,5S-isomer (threo form).

The isomers with the erythro configuration are preferred in this connection, particularly preferably the 3R,5S isomer and the 3R,5S-3S,5R-racemate.

(c) If the radical —A— stands for a group of the formula

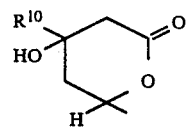

then the N-substituted pyrroles possess at least two asymmetric carbon atoms, namely the carbon atom to which the hydroxyl group is bonded, and the carbon atom to which the radical of the formula

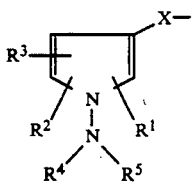

is bonded. Depending on the position of the hydroxyl group to the free valency on the lactone ring, the substituted pyrroles can be present as cis-lactones (VI) or as trans-lactones (VII)

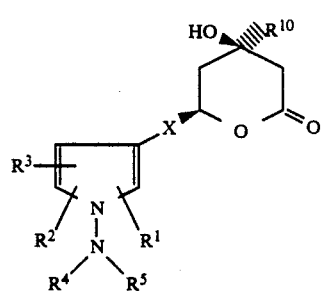

cis-lactone (VI)

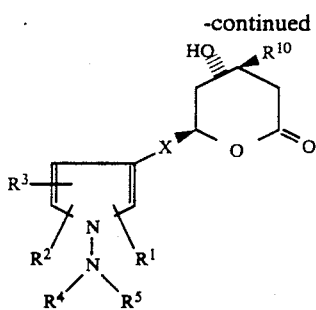

trans-lactone (VII)

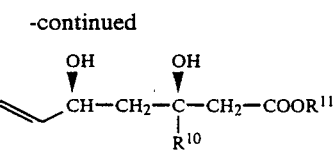

Two isomers in each case exist, in turn, both of the cis-lactone and the trans-lactone, namely the 4R,6R-isomer or the 4S,6S-isomer (cis-lactone), and the 4R,6S-isomer or 4S,6R-isomer (trans-lactone). Preferred isomers are the trans-lactones. The 4R,6S-isomer (trans) and the R,6S-4S,6R-racemate are particularly preferred in this connection.

The following isomeric forms of the substituted pyrroles may be mentioned as examples:

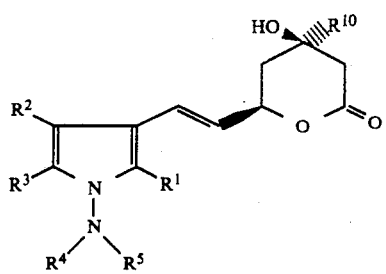

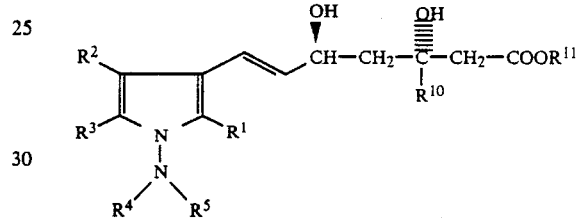

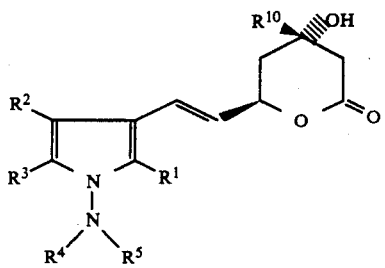

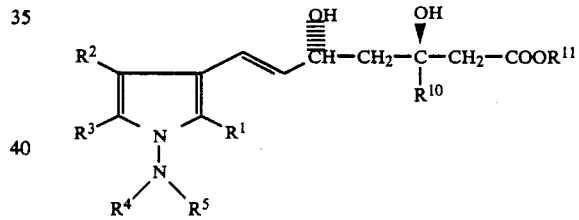

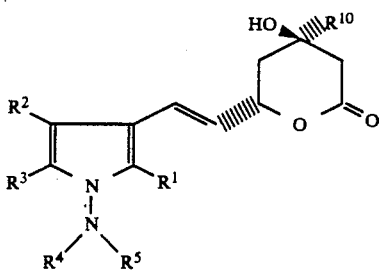

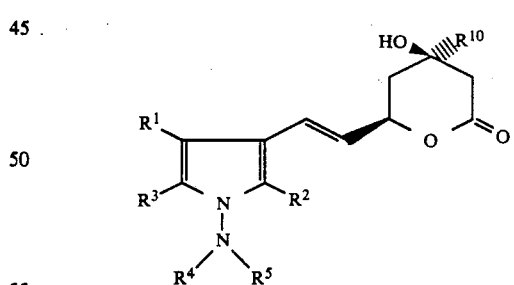

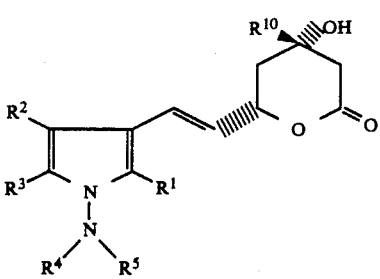

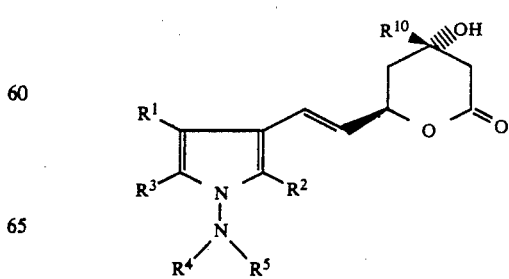

-continued

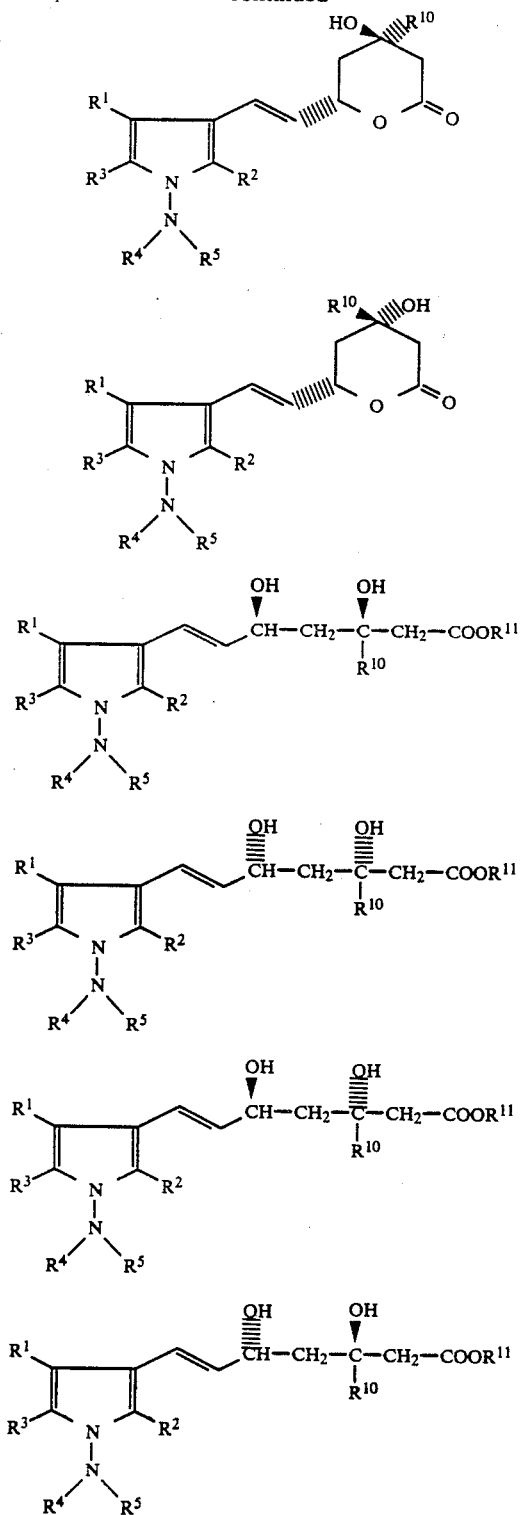

The compounds of the general formula (Ia) are very particularly preferred in which
$R^1$ stands for cyclopropyl, methyl, ethyl, propyl, isopropyl, butyl, isobutyl or tert.-butyl, each of which can be substituted by fluorine, chlorine, hydroxyl, methoxy, phenyl or phenoxy,
$R^2$ stands for phenyl which can be monosubstituted or disubstituted by identical or different methyl, ethyl, propyl, isopropyl, butyl, isobutyl, tert.-butyl, hydroxymethyl, methoxy, ethoxy, propoxy, phenoxy, benzyloxy, fluorine, chlorine, cyano or trifluoromethyl,
$R^3$ stands for hydrogen,
stands for cyclopropyl,
stands for methyl, ethyl, propyl or isopropyl, each of which can be substituted by fluorine, hydroxyl, chlorine, cyano or trifluoromethyl,
stands for phenyl which can be substituted by fluorine, chlorine, cyano, hydroxyl or trifluoromethyl,
$R^4$ and $R^5$ are identical or different and
stand for methyl, ethyl, propyl, isopropyl, butyl or tert.-butyl, or
stand for phenyl which can be monosubstituted or disubstituted by identical or different methyl, ethyl, propyl, isopropyl, methoxy, fluorine, chlorine, hydroxyl, trifluoromethyl or methoxycarbonyl, or
$R^4$ and $R^5$, together with the N atom, form a 5- to 7-membered heterocycle, where this heterocycle can be substituted by $R^9$, where
$R^9$ stands for cyclopropyl, or
for methyl, ethyl, tert.-butyl or
for pyridyl, or
stands for phenyl which can be monosubstituted or disubstituted by identical or different methyl, ethyl, propyl, fluorine, chlorine, cyano or trifluoromethyl,
X stands for a group of the formula

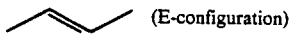 (E-configuration)

and
A stands for a group of the formula

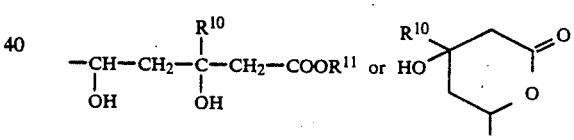

wherein
$R^{10}$ denotes hydrogen and
$R^{11}$ denotes hydrogen, methyl or ethyl or denotes a sodium or potassium cation.

In addition, a process has been found for the preparation of the substituted pyrroles of the general formula (I)

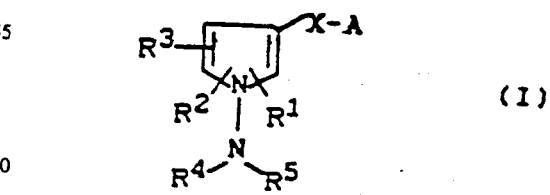

in which
$R^1$, $R^2$, $R^3$, $R^4$, $R^5$, X and A have the abovementioned meanings,
which is characterized in that ketones of the general formula (VIII)

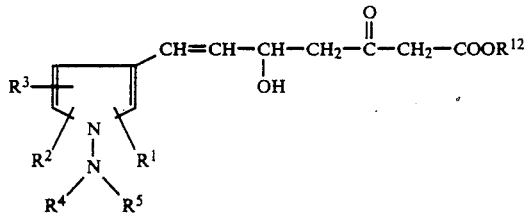

in which

R[1], R[2], R[3], R[4] and R[5] have the abovementioned meanings, and

R[12] stands for alkyl, are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$—CH$_2$—), the ethene compounds (X=—CH=—CH—) are hydrogenated by customary methods, and, if appropriate, isomers are separated.

The process according to the invention can be illustrated by the following reaction scheme:

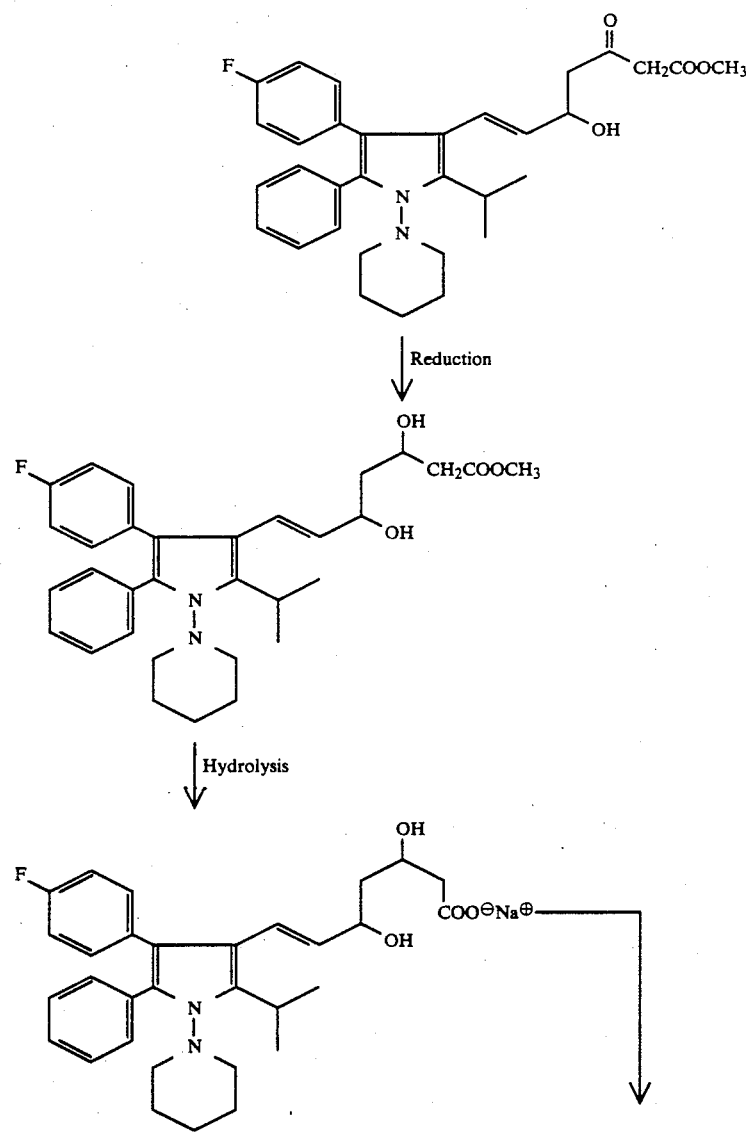

-continued

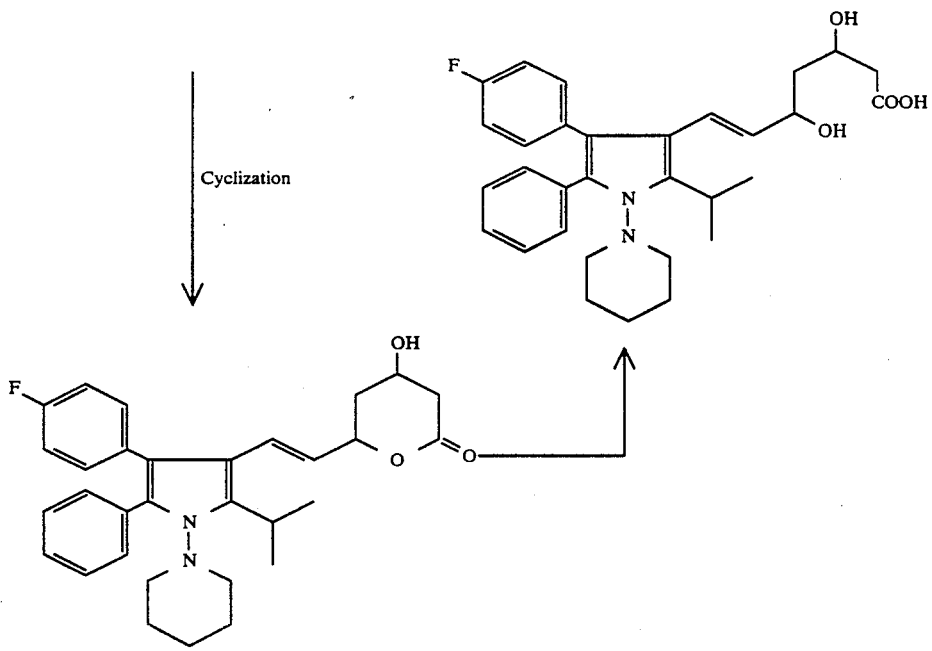

The reduction can be carried out using the customary reducing agents, preferably using those which are suitable for the reduction of ketones to hydroxyl compounds. Reduction using metal hydrides or complex metal hydrides in inert solvents, if desired in the presence of a trialkylborane, is particularly suitable in this connection. The reduction is preferably carried out using complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride. The reduction is very particularly preferably carried out using sodium borohydride, in the presence of triethylborane.

Suitable solvents in this connection are the customary organic solvents which do not change under the reaction conditions. These preferably include ethers such as, for example, diethyl ether, dioxane, tetrahydrofuran or dimethoxyethane or halogenated hydrocarbons such as, for example, dichloromethane, trichloromethane, tetrachloromethane, 1,2-dichloroethane, or hydrocarbons such as, for example, benzene, toluene or xylene. It is also possible to employ mixtures of the solvents mentioned.

The reduction of the ketone group to the hydroxyl group is particularly preferably carried out under conditions in which the other functional groups such as, for example, the alkoxycarbonyl group are not changed. The use of sodium borohydride as a reducing agent in the presence of triethylborane in inert solvents preferably such as ethers is particularly suitable for this.

The reduction is in general carried out in a temperature range from $-90°$ C. to room temperature $(+30°$ C.), preferably from $-80°$ C. to $0°$ C.

The process according to the invention is in general carried out at atmospheric pressure. However, it is also possible to carry out the process at underpressure or at overpressure (for example in a range from 0.5 to 5 bar).

In general, the reducing agent is employed in an amount from 1 to 2 moles, preferably from 1 to 1.5 moles, relative to 1 mole of the keto compound.

Under the abovementioned reaction conditions, the carbonyl group is in general reduced to the hydroxyl group without reduction of the double bond to the single bond taking place.

To prepare compounds of the general formula (I), in which X stands for an ethylene grouping, the reduction of the ketones (III) can be carried out under those conditions under which both the carbonyl group and the double bond are reduced.

Moreover, it is also possible to carry out the reduction of the carbonyl group and the reduction of the double bond in two separate steps. In this case, the double bond is preferably hydrogenated after reduction of the carbonyl group in the presence of a noble metal catalyst, such as, for example, palladium or rhodium (J. Med. Chem. 28, 347 (1985).

The carboxylic acids in the context of the general formula (I) correspond to the formula (Ic)

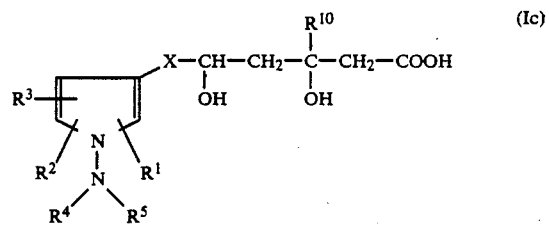

in which
$R^1$, $R^2$, $R^3$, $R^4$, $R^5$, $R^{10}$ and X have the abovementioned meanings.

The carboxylic acid esters in the context of the general formula (I) correspond to the formula (Id)

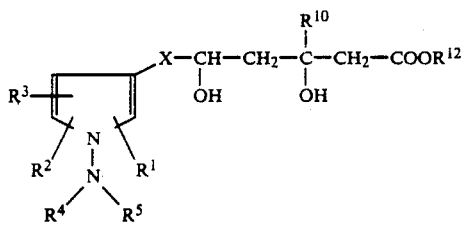

in which
R¹, R², R³, R⁴, R⁵, R¹⁰ and X have the abovementioned meanings, and
R¹² stands for alkyl.

The salts of the compounds according to the invention in the context of the general formula (I) correspond to the formula (Ie)

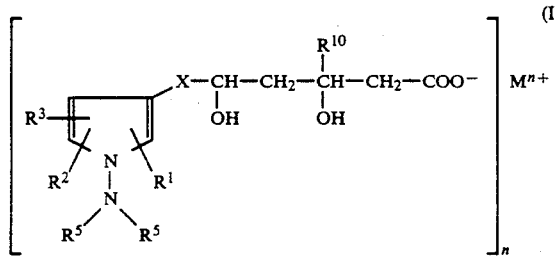

in which
R¹, R², R³, R⁴, R⁵, R¹⁰ and X have the abovementioned meanings, and
$M^{n+}$ stands for a cation.

The lactones in the context of the general formula (I) correspond to the formula (If)

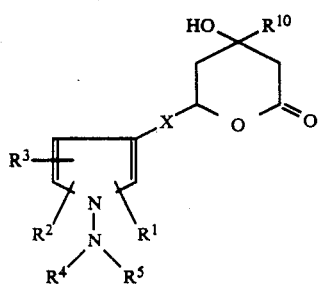

in which
R¹, R², R³, R⁴, R⁵, R¹⁰ and X have the abovementioned meanings.

To prepare the carboxylic acids of the general formula (Ic) according to the invention, the carboxylic acid esters of the general formula (Id) or the lactones of the general formula (If) are in general hydrolyzed by customary methods. The hydrolysis is in general carried out by treating the esters or the lactones with customary bases in inert solvents, by means of which the salts of the general formula (Ie) in general initially result, which can subsequently be converted in a second step into the free acids of the general formula (Ic) by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at atmospheric pressure. However, it is also possible to work at underpressure or at overpressure (for example from 0.5 to 5 bar).

When carrying out the hydrolysis, the base is in general employed in an amount from 1 to 3 moles, preferably from 1 to 1.5 moles, relative to 1 mole of the ester or the lactone. Molar amounts of the reactants are particularly preferably used.

When carrying out the reaction, the salts of the compounds (Ie) according to the invention are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. It has also proved advantageous in this connection in the preparation of the carboxylic acids (Ic) to acidify the basic reaction mixture from the hydrolysis in a second step without isolation of the salts. The acids can then be isolated in a customary manner.

To prepare the lactones of the formula (If) according to the invention, the carboxylic acids (Ic) according to the invention are in general cyclized by customary methods, for example by heating the corresponding acid in inert organic solvents, if desired in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons, in particular toluene, in the presence of molecular sieve are particularly preferably used.

The cyclization is in general carried out in a temperature range from −40° C. to +200° C., preferably −25° C. to +50° C.

The cyclization is in general carried out at atmospheric pressure, but it is also possible to carry out the process at underpressure or at overpressure (for example in a range from 0.5 to 5 bar).

Moreover, the cyclization is also carried out in inert organic solvents, with the aid of cyclizing or dehydrating agents. Carbodiimides are preferably used in this connection as dehydrating agents. N,N'-Dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably used as carbondiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene, or mineral oil fractions are particularly preferable. Chlorinated hydrocarbons such as, for example, methylene chloride, chloroform or carbon tetrachloride are particularly preferably employed.

The reaction is in general carried out in a temperature range from 0° C. to +80° C., preferably from +10° C. to +50° C.

When carrying out the cyclization, it has proved advantageous to employ the cyclization method with the aid of carbodiimides as dehydrating agents.

The resolution of the isomers into the uniform stereoisomeric constituents is in general carried out by customary methods such as, for example, described by E. L. Eliel, Stereochemistry of Carbon Compounds, McGraw Hill, 1962. In this connection, the resolution of the isomers at the racemic lactone stage is preferred. The racemic mixture of the trans-lactones (VII) is particularly preferably converted in this connection by treating either with D-(+)- or L-(−)-α-methylbenzylamine by customary methods into the diastereomeric dihydroxyamides (Ig)

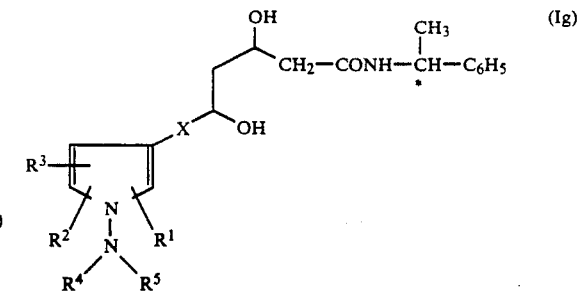

which can subsequently be separated into the individual diastereomers by chromatography or crystallization, as customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, yield the corresponding pure enantiomeric dihydroxy acids (Ic) which can be converted into the pure enantiomeric lactones by cyclization as described above. In general, it applies for the preparation of the compounds of the general formula (I) according to the invention in pure enantiomeric form that the configuration of the final product according to the method described above is dependent on the configuration of the starting materials.

The resolution of isomers is illustrated in the following reaction scheme:

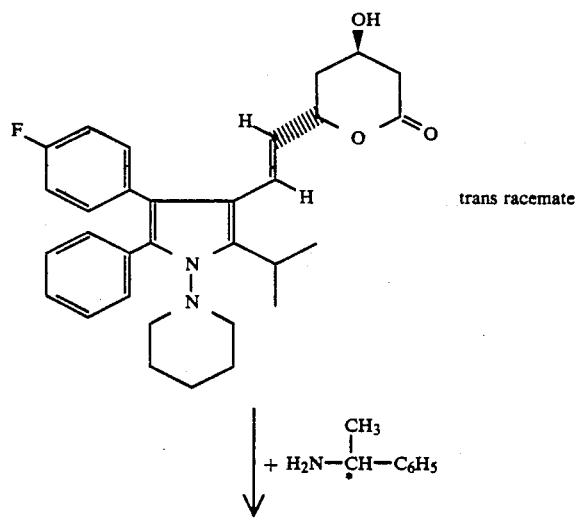

-continued

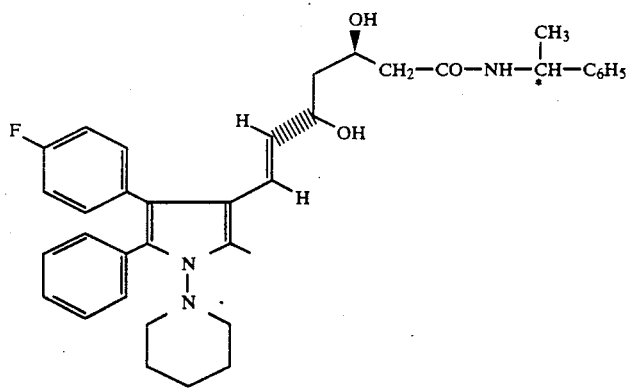

(1) resolution of diastereomers
(2) hydrolysis
(3) lactonization

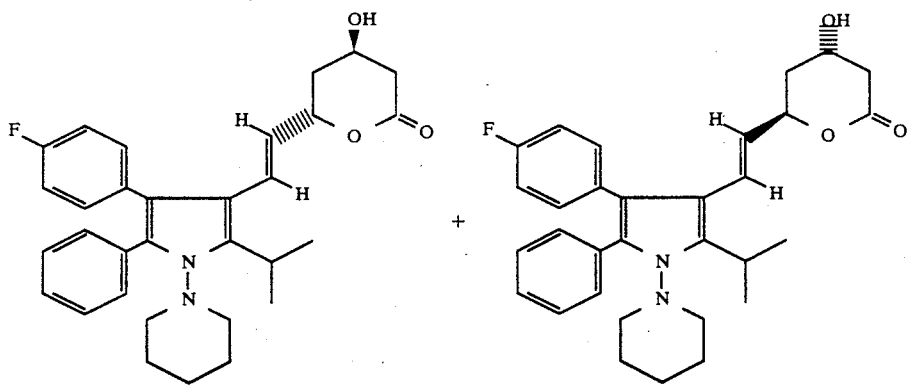

The ketones (VIII) employed as starting materials are new.

A process for the preparation of the ketones according to the invention of the general formula (VIII)

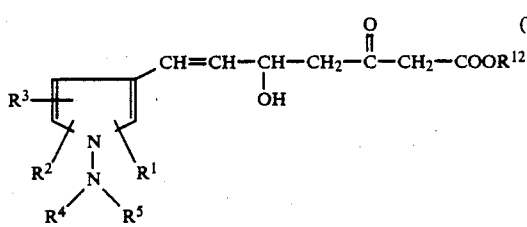

(VIII)

in which
R$^1$, R$^2$, R$^3$, R$^4$, R$^5$ and R$^{12}$ have the abovementioned meanings,
has been found, which is characterized in that aldehydes of the general formula (IX)

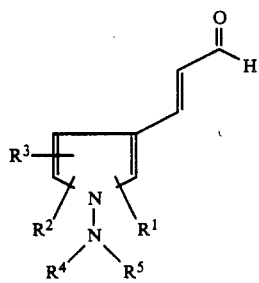

(IX)

in which
R$^1$, R$^2$, R$^3$, R$^4$ and R$^5$ have the abovementioned meanings,
are reacted in inert solvents with acetoacetates of the general formula (X)

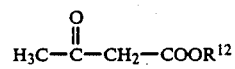

(X)

in which
R$^{12}$ has the abovementioned meaning,
in the presence of bases.

The process according to the invention can be illustrated, for example, by the following reaction:

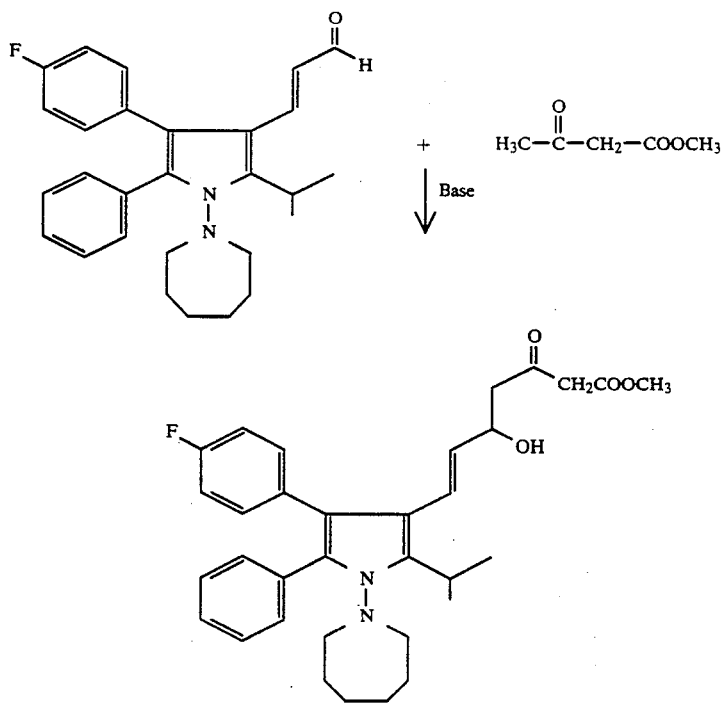

Suitable bases in this connection are the customary strong basic compounds. These preferably include organolithium compounds such as, for example, n-butyllithium, sec.butyllithium, tert.butyllithium or phenyllithium, or amides such as, for example, lithium diisopropylamide, sodium amide or potassium amide, or lithium hexamethyldisilylamide, or alkali metal hydrides such as sodium hydride or potassium hydride. It is also possible to employ mixtures of the bases mentioned. n-Butyllithium or sodium hydride or their mixture is particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range from $-80°$ C. to $+50°$ C., preferably from $-20°$ C. to room temperature.

The process is in general carried out at atmospheric pressure, but it is also possible to carry out the process at underpressure or at overpressure, for example in a range from 0.5 to 5 bar.

When carrying out the process, the acetoacetate is in general employed in an amount from 1 to 2, preferably from 1 to 1.5, moles relative to 1 mole of the aldehyde.

The acetoacetates of the formula (X) employed as starting materials are known or can be prepared by known methods [Beilstein's Handbuch der organischen Chemie (Beilstein's Handbook of Organic Chemistry) III, 632; 438].

Examples of acetoacetates which may be mentioned for the process according to the invention are methyl acetoacetate, ethyl acetoacetate, propyl acetoacetate and isopropyl acetoacetate.

The aldehydes of the general formula (IX) employed as starting materials are new.

A process for the preparation of the aldehydes of the general formula (IX)

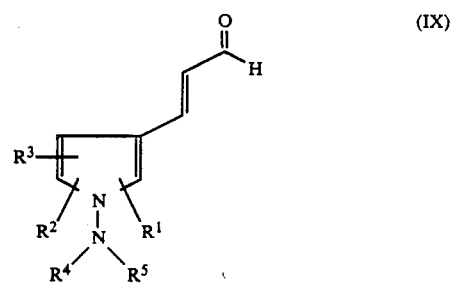

in which
R$^1$, R$^2$, R$^3$, R$^4$ and R$^5$ have the abovementioned meanings,
has additionally been found, which is characterized in that pyrroles of the general formula (XI)

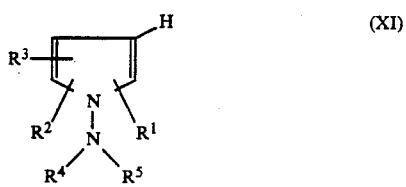

in which
R$^1$, R$^2$, R$^3$, R$^4$ and R$^5$ have the abovementioned meanings,
are reacted in inert solvents in the presence of acid halides with N,N-dialkylaminoacrolein of the formula (XII)

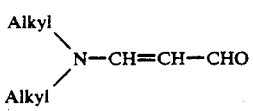

(XII)

wherein
alkyl stands for a straight-chain or branched hydrocarbon radical ($C_1$ to $C_4$).

The process according to the invention can be illustrated, for example, by the following equation:

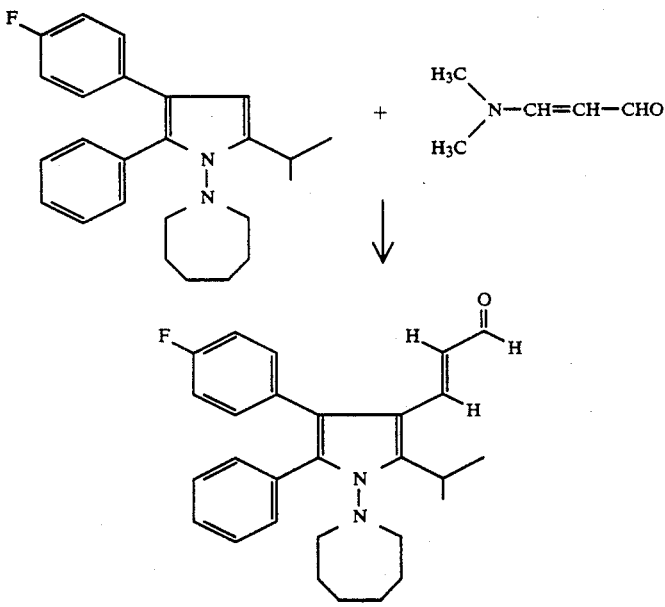

Suitable solvents in this connection are the customary organic solvents which are stable under the reaction conditions. These preferably include hydrocarbons such as benzene, toluene, xylene, hexane, mineral oil fractions, halogenated hydrocarbons, such as chlorobenzene or dichlorobenzene, or ethers such as diethyl ether, dioxane or tetrahydrofuran, or chlorinated hydrocarbons, such as methylene chloride, chloroform or carbon tetrachloride, or acetonitrile. It is also possible to employ mixtures of the solvents mentioned. Anhydrous acetonitrile or chloroform are particularly preferably used.

Acid chlorides are in general used as auxiliaries. Phosphorus oxychloride or phosgene, particularly preferably phosphorus oxychloride, is preferably employed.

The reaction is in general carried out in a temperature range from −20° C. to +150° C., preferably from 0° C. to +100° C.

The process is in general carried out at atmospheric pressure. However, it is also possible to carry out the process at underpressure or at overpressure (for example in a range from 0.5 to 5 bar).

When carrying out the process, the dimethylaminoacrolein is in general employed in an amount from 2 to 6, preferably from 3 to 4, moles relative to 1 mole of the pyrrole.

The pyrroles of the general formula (XI) employed as starting materials are known or can be prepared by known methods [A. Glossauer "Die Chemie der Pyrrole" ("The Chemistry of Pyrroles"), Springer Verlag Berlin, 1974].

The N-substituted N-amino-pyrroles according to the invention possess valuable pharmacological properties and can be employed as active compounds in medicaments. In particular, they are inhibitors of 3-hydroxy-3-methylglutarylcoenzyme A (HGM-CoA) reductase and inhibitors of cholesterol biosynthesis. They can be employed for the treatment of hyperlipoproteinaemia, lipoproteinaemia or arteriosclerosis. The active compounds according to the invention also effect a reduction of the cholesterol content in the blood.

The new active compounds can be converted in a known manner into the customary formulations, such as tablets, dragees, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compound using solvents and/or excipients, if appropriate using emulsifiers and/or dispersants, where, for example, in the case of the use of water as diluents, if appropriate organic solvents can be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration takes place in a customary manner, preferably orally, parenterally, perlingually or intravenously. In the case of oral administration, the tablets can, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions, various flavor improvers or colorants can be added to the active compounds in addition to the abovementioned auxiliaries.

In the case of parenteral administration, solutions of the active compounds can be employed using suitable liquid excipients.

In general it has proved advantageous on intravenous administration to administer amounts of about 0.001 to 1 mg/kg, preferably about 0.01 to 0.5 mg/kg of body weight to obtain effective results, and on oral administration, the dosage is about 0.01 to 20 mg/kg, preferably 0.1 to 10 mg/kg of body weight.

In spite of this, it may sometimes be necessary to deviate from the amounts mentioned, depending on the body weight or the type of administration route, on individual behaviour towards the medicament, the manner of its formulation and the point in time or interval at which administration takes place. Thus, in some cases it may be sufficient to manage with less than the previously mentioned minimum amount, whereas in other cases the upper limit mentioned must be exceeded. In the case of the administration of larger amounts, it may be advisable to divide these into several individual doses over the day.

Starting Compounds and Preparation Examples

EXAMPLE 1

1-(4-Fluorophenyl)-4-methyl-pent-1-en-3-one

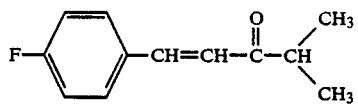

75 ml of 15% strength potassium hydroxide solution are added dropwise to 198.4 g (1.6 mol) of freshly distilled 4-fluorobenzaldehyde and 137.6 g (1.6 mol) of methyl isopropyl ketone in 300 ml of methanol and the mixture is stirred overnight at room temperature. It is then neutralized using 10 ml of acetic acid, 1 l of water is added and the mixture is extracted using two 500 ml portions of ether. The combined organic phases are washed with 500 ml of saturated sodium chloride solution and dried over sodium sulphate. After stripping off the solvent, the residue is distilled in a high vacuum.

Yield: 198.6 g (65% of theory) of yellowish oil
b.p.: 103° C. (0.3 mbar)

$^1$H-NMR (CDCl$_3$): δ=1.2 (d, 6H, CH$_3$); 2.9 (sept, 1H, CH—(CH$_3$)$_2$); 6.8 (d, 1H, olefin H); 7.1 (m, 2H, aromatic H); 7.6 (m, 3H, aromatic H+olefin H).

EXAMPLE 2

2-(4-Fluorophenyl)-5-methyl-1-phenyl-hexane-1,4-dione

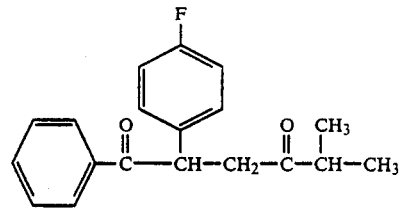

A solution of 63.6 g (0.6 mol) of freshly distilled benzaldehyde in 300 ml of dimethylformaldehyde is added dropwise during the course of 30 minutes to a solution of 5.88 g (0.12 mol) of sodium cyanide in 300 ml of dimethylformamide at 35° C. and the mixture is stirred for a further 5 minutes at this temperature. 86.5 g (0.45 mol) of 1-(4-fluorophenyl)-4-methyl-pent-1-en-3-one (Example 1) in 500 ml of dimethylformamide are then added dropwise within the course of 1.5 hours and the mixture is subsequently stirred for 1 hour, the temperature always being kept at 35° C.

After adding 1 l of water, the mixture is extracted four times using 400 ml of chloroform each time, and the combined organic phases are washed with 1 l of saturated sodium hydrogen carbonate solution and 1 l of water and dried over sodium sulphate. After concentrating in vacuo, the residue is distilled under reduced pressure until finally a fraction passes over at 138°-142° C. (0.9 mbar). The distillation residue (132 g) is now chromatographed in two portions on a column (1.5 kg of silica gel 230-400 mesh, φ9 cm), using petroleum ether/ethyl acetate (10:1). The product is obtained after 4-7 l of eluent. After stripping off the solvent, 90.0 g (67 % of theory) of colorless oil remain.

$^1$H-NMR (CDCl$_3$): δ=1.08 (d, 3H, CH$_3$); 1.12 (d, 3H, CH$_3$); 2.65 (sept, 1H, CH—(CH$_3$)$_2$); 2.7 (dd, 1H, —CO—CH$_2$—CH); 3.6 (dd, 1H, —CO—CH$_2$—CH); 5.12 (dd, 1H, H—C—C$_6$H$_4$—F); 6.95 (m, 2H, aromatic H); 7.23 (m, 2H, aromatic H); 7.4 (m, 3H, aromatic H); 7.95 (m, 2H, aromatic H).

EXAMPLE 3

3-(4-Fluorophenyl)-5-isopropyl-2-phenyl-1-(1-pyrrolidinyl)pyrrole

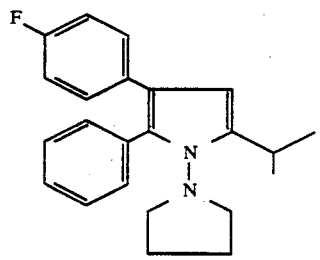

20 g of molecular sieve 3 Å are added to 15 g (50 mmol) of the compound from Example 2 and 20 g (164 mmol) of N-aminopyrrolidine hydrochloride in 150 ml of toluene AR and the mixture is heated to reflux for 48 hours. The mixture is cooled, filtered and washed well with toluene. The toluene solutions are combined and extracted 3× using 1N hydrochloric acid. The organic phase is subsequently washed using saturated sodium hydrogen carbonate solution, dried over magnesium sulphate and concentrated in vacuo. The residue is stirred with a little ethanol, cooled and filtered off with suction. After drying in a desiccator, 2.3 g of substance are obtained.

Yield: 12.8 % of theory $^1$H-NMR (CDCl$_3$): δ=1.31 (d, 6H); 1.5-1.8 (m, 4H); 3.05 (m, 1H); 3.23 (m, 4H); 6.03 (s, 1H); 6.8 (m, 2H); 7.07 (m, 2H); 7.35 (m, 5H).

EXAMPLE 4

(E)-3-[3-(4-Fluorophenyl)-5-isopropyl-2-phenyl-1-(1-pyrrolidinyl)-pyrrol-4-yl]-prop-2-enal

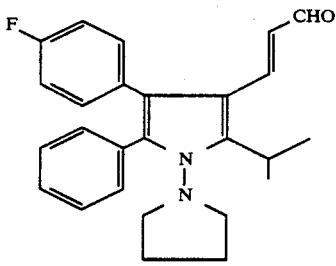

1.9 g (17.9 mmol) of 90% strength 3-dimethylaminoacrolein in 30 ml of acetonitrile AR are added dropwise under nitrogen to 1.8 ml (19.2 mmol) of freshly distilled phosphorus oxychloride in 20 ml of acetonitrile AR at −5° C. The mixture is subsequently stirred for 10 minutes and 2.3 g (6.4 mmol) of the compound from Example 3 dissolved in 20 ml of acetonitrile AR and 30 ml of tetrahydrofuran AR are then added dropwise at the same temperature. The mixture is subsequently heated to reflux overnight and cooled to room temperature. The batch is added to a mixture of 4.7 g of sodium hydroxide in 300 ml of toluene/water 1:1 in such a way that the temperature does not exceed 10° C. The mixture is subsequently stirred for 10 minutes, the organic phase is separated off and the aqueous phase is extracted twice using ethyl acetate. The organic phases are combined, washed with saturated sodium chloride solution and dried over magnesium sulphate. After concentrating in vacuo, the residue is stirred with ethyl acetate/petroleum ether 1:1, filtered off with suction and dried in a desiccator.

Yield: 2 g (71.4% of theory).

$^1$H-NMR (CDCl$_3$): δ=1.48 (d, 6H); 1.72 (m, 4H); 3.23 (m, 4H); 3.5 (m, 1H); 5.75 (dd, 1H); 6.85 (m, 2H); 7.05 (m, 2H); 7.25 (m, 5H); 7.55 (d, 1H); 9.38 (d, 1H).

EXAMPLE 5

Methyl (E)-7-[3-(4-fluorophenyl)-5-isopropyl-2-phenyl-1-(1-pyrrolidinyl)-pyrrol-4-yl]-5-hydroxy-3-oxo-hept-6-enoate

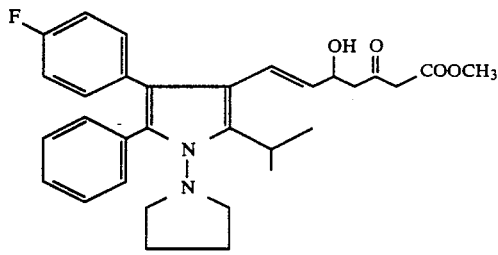

1.1 ml (10 mmol) of methyl acetoacetate in 5 ml of dry tetrahydrofuran are added dropwise under nitrogen to a suspension of 360 mg (12 mmol) of 80% strength sodium hydride in 30 ml of dry tetrahydrofuran at −5° C. After 15 minutes, 6.2 ml (10 mmol) of 15% strength butyllithium in n-hexane are added dropwise at the same temperature and the mixture is subsequently stirred for 15 minutes. 2 g (5 mmol) of the compound from Example 4, dissolved in 20 ml of dry tetrahydrofuran, are subsequently added dropwise and the mixture is subsequently stirred for 30 minutes at −5° C. 3.3 ml of 50% strength acetic acid are cautiously added to the reaction solution, it is diluted with 100 ml of water and the mixture is extracted three times using 100 ml of ether each time. The combined organic phases are washed twice with saturated sodium hydrogen carbonate solution and once with saturated sodium chloride solution, dried over magnesium sulphate and concentrated in vacuo. The residue is chromatographed on a column (silica gel 70-230 mesh, using ethyl acetate/petroleum ether 4:6).

Yield: 1 g (40% of theory)

$^1$H-NMR (CDCl$_{13}$): δ=1.42 (d, 6H); 1.50 (m, 2H); 1.72 (m, 2H); 2.62 (m, 2H); 3.22 (m, 4H); 3.32 (m, 1H); 3.46 (s, 2H); 3.73 (s, 3H); 4.55 (m, 1H); 5.12 (dd, 1H); 6.62 (d, 1H); 6.82 (m, 2H); 7.03 (m, 2H); 7.23 (m, 5H).

EXAMPLE 6

Methyl erythro-(E)-7-[3-(4-fluorophenyl)-5-isopropyl-2-phenyl-1-(1-pyrrolidinyl)-pyrrol-4-yl]-3,5-dihydroxy-hept-6-enoate

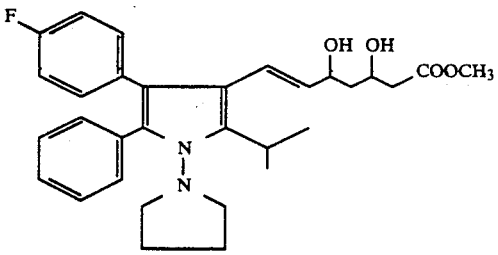

2.4 ml (2.4 mmol) of a 1 molar triethylborane solution in tetrahydrofuran are added at room temperature to a solution of 1 g (1.93 mmol) of the compound from Example 5 in 30 ml of dry tetrahydrofuran, air is passed through the solution during 5 minutes and it is cooled to an internal temperature of −30° C. 91 mg (2.4 mmol) of sodium borohydride and, slowly, 1.8 ml of methanol are added, the mixture is stirred for 30 minutes at −30° C. and then a mixture of 8.5 ml of 30% strength hydrogen peroxide and 17 ml of water is added. The temperature is allowed to climb to 0° C. during this and the mixture is subsequently stirred for a further 30 minutes. The mixture is extracted three times using 50 ml of ethyl acetate each time, and the combined organic phases are washed once each with saturated sodium hydrogen carbonate solution and saturated sodium chloride solution, dried over magnesium sulphate and concentrated in vacuo. The residue is chromatographed on a column (silica gel 230–400 mesh, using ethyl acetate/petroleum ether 1:1).

Yield: 400 mg (40% of theory).

$^1$H-NMR (CDCl$_3$): δ=1.42 (d, 6H); 1.40–1.80 (m, 6H); 2.47 (m, 2H); 3.22 (m, 4H); 3.32 (m, 1H); 3.70 (s, 3H); 4.22 (m, 1H); 4.37 (m, 1H); 5.17 (dd, 1H); 6.58 (d, 1H); 6.80 (m, 2H); 7.03 (m, 2H); 7.23 (m, 5H).

EXAMPLE 7

3-(4-Fluorophenyl)-5-isopropyl-2-phenyl-1-piperidinopyrrole

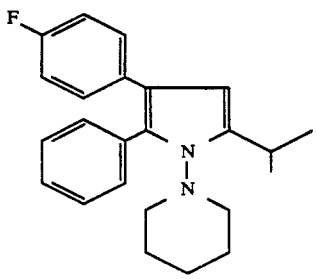

7.5 ml of conc. hydrochloric acid are added to 22.5 g (75 mmol) of the compound from Example 2 and 25 g (250 mmol) of N-aminopiperidine in 200 ml of toluene AR and 30 ml of dimethylformamide and the mixture is heated to reflux in a water separator for 48 hours. The mixture is cooled, diluted using 200 ml of ethyl acetate, and extracted three times using 1N hydrochloric acid and twice using saturated sodium hydrogen carbonate solution. The organic phase is dried over magnesium sulphate and concentrated in vacuo, and the residue is chromatographed on a column (silica gel 70–230 mesh, using ethyl acetate/petroleum ether 95:5).

Yield: 7.2 g (26.5% of theory).

$^1$H-NMR (CDCl$_3$): δ=1.0 (m, 1H); 1.26 (d, 6H); 1.35–1.6 (m, 5H); 2.88 (m, 2H); 3.1 (m, 3H); 5.95 (s, 1H); 6.75 (m, 2H); 7.0 (m, 2H); 7.31 (m, 5H).

EXAMPLE 8

(E)-3-[3-(4-Fluorophenyl)-5-isopropyl-2-phenyl-1-piperidino-pyrrol-4-yl]-prop-2-enal

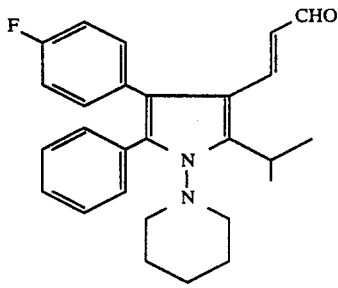

7.2 g (20 mmoL) of the compound from Example 7 are reacted analogously to Example 4.

Yield: 7.2 g (86.7% of theory).

$^1$H-NMR (CDCl$_3$): δ=0.93 (m, 1H); 1.48 (d, 6H); 1.5–1.7 (m, 5H); 2.92 (m, 2H); 3.15 (m, 2H); 3.55 (m, 1H); 5.75 (dd, 1H); 6.83 (m, 2H); 7.0 (m, 2H); 7.25 (m, 5H); 7.52 (d, 1H); 9.37 (d, 1H).

EXAMPLE 9

Methyl (E)-7-[3-(4-fluorophenyl-5-isopropyl-2-phenyl-1-piperidino-pyrrol-4-yl]-5-hydroxy-3-oxo-hept-6-enoate

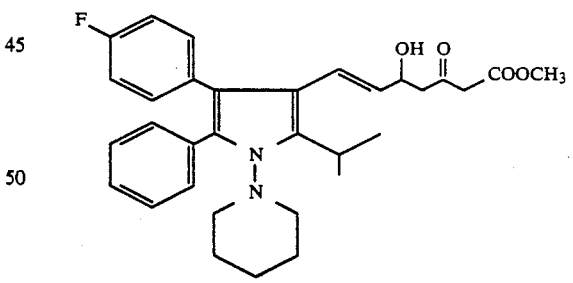

7.2 g (17.3 mmol) of the compound from Example 8 are reacted analogously to Example 5.

Yield: 6.2 g (67.4% of theory).

$^1$H-NMR (CDCl$_3$): δ=1.40 (d, 6H); 0.90–1.60 (m, 6H); 2.62 (m, 2H); 2.90 (m, 2H); 3.12 (m, 2H); 3.38 (m, 1H); 3.47 (s, 2H); 3.73 (s, 3H); 4.53 (m, 1H); 5.15 (dd, 1H); 6.54 (d, 1H); 6.80 (m, 2H); 7.01 (m, 2H); 7.25 (m, 5H).

EXAMPLE 10

Methyl erythro-(E)-7-[3-(4-fluorophenyl)-5-isopropyl-2-phenyl-1-piperidino-pyrrol-4-yl]-3,5-dihydroxy-hept-6-enoate

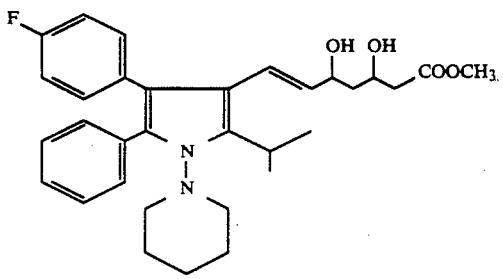

6.2 g (11.7 mmol) of the compound from Example 9 are reacted analogously to Example 6.

Yield: 4.3 g (69.4% of theory).

$^1$H-NMR (CDCl$_3$): δ=1.42 (d, 6H); 0.90–1.70 (m, 8H); 2.47 (m, 2H); 2.92 (m, 2H); 3.13 (m, 2H); 3.41 (m, 1H); 3.72 (s, 3H); 4.20 (m, 1H); 4.36 (m, 1H); 5.19 (dd, 1H); 6.52 (d, 1H); 6.78 (m, 2H); 7.02 (m, 2H); 7.23 (m, 5H).

EXAMPLE 11

1-(4-Fluoro-3-phenoxyphenyl)-4-methyl-pent-1-en-3-one

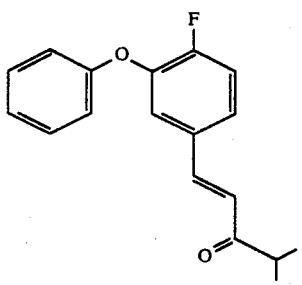

14.1 ml of 15% strength aqueous potassium hydroxide solution are added to 64.8 g (0.3 mol) of 3-phenoxy-4fluorobenzaldehyde and 51.6 g (0.6 mol) of methyl isopropyl ketone in 90 ml of methanol and the mixture is stirred overnight at room temperature. The mixture is neutralized using 1.95 ml of glacial acetic acid, diluted using 300 ml of water and extracted a number of times using ether. The organic phase is dried over magnesium sulphate and concentrated in vacuo, and the residue is chromatographed on a column (silica gel 70–230 mesh, using ethyl acetate/petroleum ether 1:9).

Yield: 41.6 g (48.8% of theory).

EXAMPLE 12

2-(4-Fluoro-3-phenoxyphenyl)-5-methyl-1-phenyl-hexan-1,4-dione

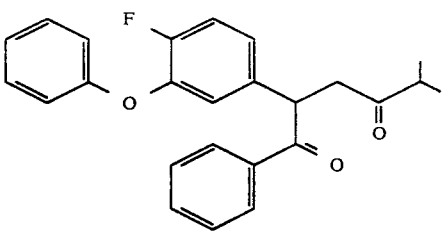

12.5 g (44 mmol) of the compound from Example 11 are reacted analogously to Example 2.

Yield: 9.5 g (55.5% of theory).

EXAMPLE 13

3-(4-Fluoro-3-phenoxyphenyl)-5-isopropyl-2-phenyl-1-piperidino-pyrrole

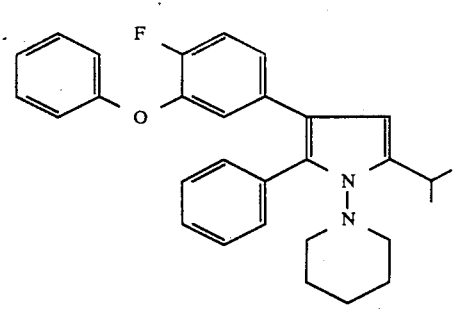

18.45 g (47.4 mmol) of the compound from Example 12 are reacted analogously to Example 7.

Yield: 5.1 g (23.7% of theory).

$^1$H-NMR (CDCl$_3$): δ=1.0 (m, 1H); 1.28 (d, 6H); 1.4–1.6 (m, 5H); 2.89 (m, 2H); 3.1 (m, 3H); 5.95 (s, 1H); 6.2–7.35 (m, 13H).

EXAMPLE 14

(E)-3-[3-(4-Fluoro-3-phenoxyphenyl)-5-isopropyl-2-phenyl-1-piperidino-pyrrol-4-yl]-prop-2-enal

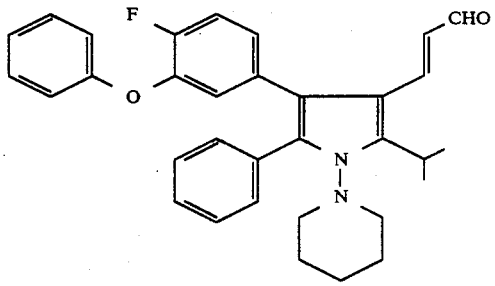

5.1 g (11.2 mmol) of the compound from Example 13 are reacted analogously to Example 4.

Yield: 5 g (87.7% of theory).

$^1$H-NMR (CDCl$_3$): δ=0.9 (m, 1H); 1.45 (m, 6H); 1.52 (m, 5H); 2.9 (m, 2H); 3.1 (m, 2H); 3.5 (m, 1H); 5.81 (dd, 1H); 6.7–7.35 (m, 13H); 7.5 (d, 1H); 9.4 (d, 1H).

EXAMPLE 15

Methyl (E)-7-[3-(4-fluoro-3-phenoxyphenyl)-5-isopropyl-2-phenyl-1-piperidino-pyrrol-4-yl]-5-hydroxy-3-oxo-hept-6-enoate

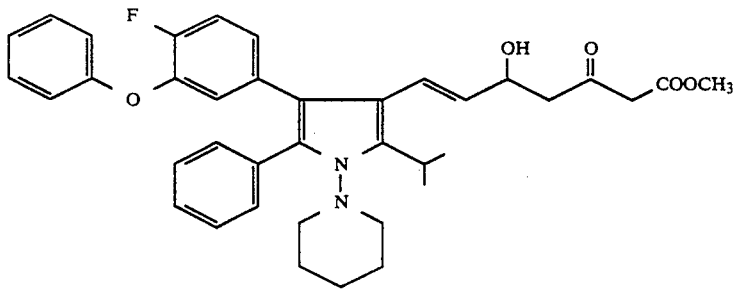

5 g (9.8 mmol) of the compound from Example 14 are reacted analogously to Example 5.

Yield: 3.5 g (57.3% of theory).

$^1$H-NMR (CDCl$_3$): δ=1.37 (d, 6H); 0.90–1.60 (m, 6H); 2.62 (m, 2H); 2.87 (m, 2H); 3.08 (m, 2H); 3.37 (m, 1H); 3.45 (s, 2H); 3.73 (s, 3H); 4.54 (m, 1H); 5.22 (dd, 1H); 6.52 (d, 1H); 6.71 (m, 2H); 6.78 (m, 1H); 6.92 (m, 1H); 7.02 (m, 1H); 7.23 (m, 8H).

EXAMPLE 16

Methyl erythro-(E)-7-[3-(4-fluoro-3-phenoxyphenyl)-5-isopropyl-2-phenyl-1-piperidino-pyrrol-4-yl]-3,5-dihydroxy-hept-6-enoate

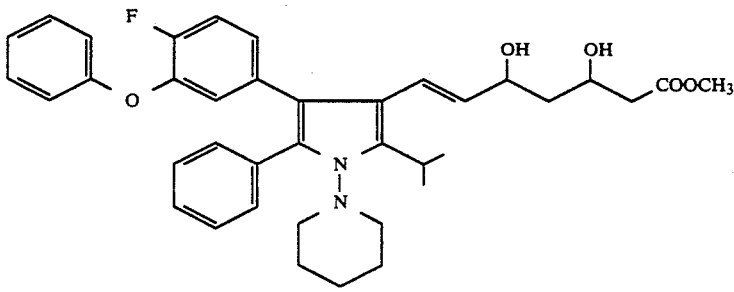

3.5 g (5.6 mmol) of the compound from Example 15 are reacted analogously to Example 6.

Yield: 2.3 g (65.5% of theory).

$^1$H-NMR (CDCl$_3$): δ=1.37 (d, 6H); 0.9–1.7 (m, 8H); 2.47 (m, 2H); 2.90 (m, 2H); 3.12 (m, 2H); 3.38 (m, 1H); 3.72 (s, 3H); 4.22 (m, 1H); 4.37 (m, 1H); 5.26 (dd, 1H); 6.51 (d, 1H); 6.65–7.10 (m, 5H); 7.25 (m, 8H).

EXAMPLE 17

3-(4-Fluoro-3-phenoxyphenyl)-6-methyl-heptan-2,5-dione

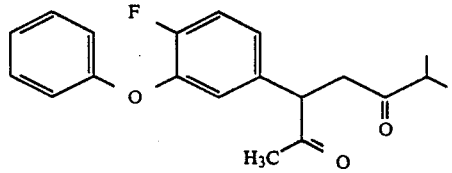

3 ml (42.2 mmol) of nitroethane are added at 0° C. to 10 g (35.2 mmol) of the compound from Example 11 in 30 ml of acetonitrile AR. 2.77 g (17.6 mmol) of 1,8-diazabicyclo(5,4,0)undec-7-ene, dissolved in 10 ml of acetonitrile AR, are subsequently added dropwise at the same temperature and the mixture is subsequently stirred for 1 hour at room temperature. 35 ml of 0.5N hydrochloric acid are added to the batch, it is extracted a number of times using dichloromethane and the organic phase is dried over magnesium sulphate. After concentrating in vacuo, an oily residue is obtained which is taken up in 35 ml of ethanol and a solution of 1.7 g (42.2 mmol) of sodium hydroxide in 21 ml of water is added. This mixture is added dropwise at 0° C. to 4.68 ml (88 mmol) of conc. sulphuric acid in 35 ml of water and is stirred for 30 minutes at room temperature. The mixture is diluted using water and extracted a number of times using ether. The organic phase is washed twice each with 1N hydrochloric acid and saturated sodium hydrogen carbonate solution, dried over magnesium sulphate and concentrated in vacuo. After chromatography on a column (silica gel 70–230 mesh, using ethyl acetate/petroleum ether 2:8), 4.8 g of substance are obtained.

Yield: 41.5% of theory.

$^1$H-NMR (CDCl$_3$): δ=1.05 (d, 3H); 1.1 (d, 3H); 2.15 (s, 3H); 2.58 (m, 2H); 3.35 (m, 1H); 4.15 (m, 1H); 6.85–7.38 (m, 8H).

EXAMPLE 18

3-(4-Fluoro-3-phenoxyphenyl)-5-isopropyl-2-methyl-1-piperidino-pyrrole

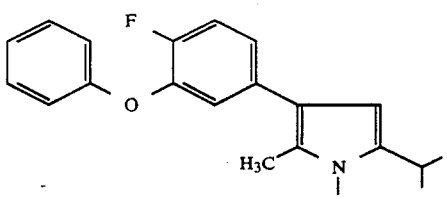

11.2 g (34 mmol) of the compound from Example 17 are reacted analogously to Example 7.
Yield: 4.2 g (31.5% of theory).
$^1$H-NMR (CDCl$_3$): δ=1.22 (d, 6H); 1.30 (m, 1H); 1.72 (m, 5H); 2.38 (s, 3H); 3.06 (m, 1H); 3.15 (m, 2H); 3.30 (m, 2H); 5.77 (s, 1H); 7.0–7.40 (m, 8H).

EXAMPLE 19

(E)-3-[3-(4-Fluoro-4-phenoxyphenyl)-5-isopropyl-2-methyl-1-piperidino-pyrrol-4-yl]-prop-2-enal

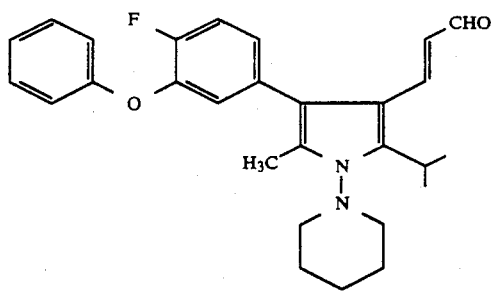

4.15 g (10.6 mmol) of the compound from Example 18 are reacted analogously to Example 4.
Yield: 2 g (42.6% of theory).
$^1$H-NMR (CDCl$_3$): δ=1.30 (m, 1H); 1.38 (d, 6H); 1.73 (m, 5H); 2.18 (s, 3H); 3.13 (m, 2H); 3.32 (m, 2H); 3.43 (m, 1H); 5.73 (dd, 1H); 6.70–7.45 (m, 8H); 7.40 (d, 1H); 9.33 (d, 1H).

EXAMPLE 20

Methyl (E)-7-[3-(4-fluoro-3-phenoxyphenyl)-5-isopropyl-2-methyl-1-piperidino-pyrrol-4-yl]-5-hydroxy-3-oxo-hept-6-enoate

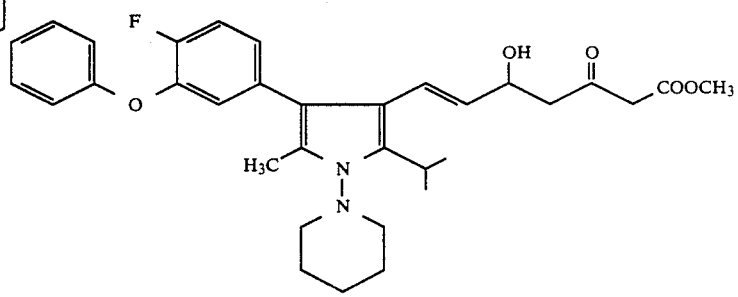

2 g (4.5 mmol) of the compound from Example 19 are reacted analogously to Example 5.
Yield: 1.7 g (67.2% of theory).
$^1$H-NMR (CDCl$_3$): δ=1.32 (d, 6H); 1.20–1.80 (m, 6H); 2.22 (s, 3H); 2.62 (m, 2H); 3.13 (m, 2H); 3.30 (m, 3H); 3.46 (3, 2H); 3.73 (s, 3H); 4.52 (m, 1H); 5.18 (dd, 1H); 6.45 (d, 1H); 6.90–7.40 (m, 8H).

EXAMPLE 21

Methyl erythro-(E)-7-[3-(4-fluoro-3-phenoxyphenyl)-5-isopropyl-2-methyl-1-piperidino-pyrrol-4-yl]-3,5-dihydroxy-hept-5-enoate

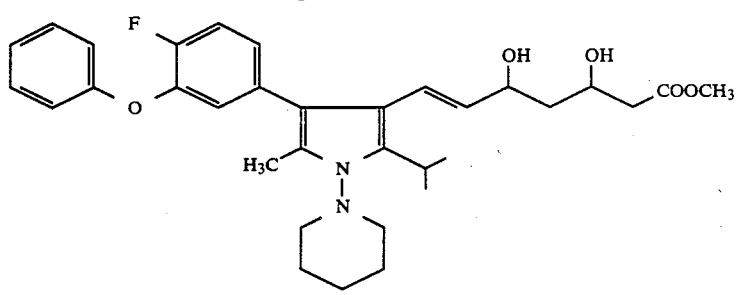

1.7 g (3 mmol) of the compound from Example 20 are reacted analogously to Example 6.
Yield: 330 mg (19.5% of theory).
$^1$H-NMR (CDCl$_3$): δ=1.32 (d, 6H); 1.20–1.80 (m, 8H); 2.20 (s, 3H); 2.47 (m, 2H); 3.15 (m, 2H); 3.30 (m, 3H); 3.71 (s, 3H); 4.22 (m, 1H); 4.33 (m, 1H); 5.19 (dd, 1H); 6.40 (d, 1H); 6.90–7.20 (m, 6H); 7.30 (m, 2H).

EXAMPLE 22

3-(4-Fluorophenyl)-1-hexahydroazepinyl-5-isopropyl-2-phenyl-pyrrole

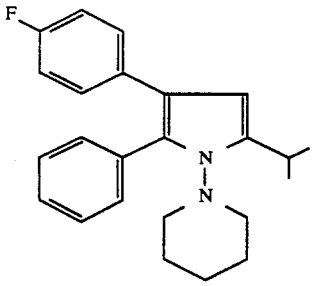

1.7 ml of conc. hydrochloric acid are added to 5 g (16.7 mmol) of the compound from Example 2 and 5.7 g (50.1 mmol) of N-amino-hexahydroazepine in 100 ml of toluene AR and 80 ml of dimethylformamide and the mixture is boiled in a water separator for 24 hours. The mixture is cooled, diluted using 200 ml of ethyl acetate and extracted three times using 1N hydrochloric acid and twice using saturated sodium hydrogen carbonate solution. The organic phase is dried over magnesium sulphate and concentrated in vacuo, and the residue is chromatographed on a column (silica gel 70–230 mesh, using ethyl acetate/petroleum ether 1:9).

Yield: 560 mg (8.9% of theory).

$^1$H-NMR (CDCl$_3$): δ=1.32 (d, 6H); 1.35–1.7 (m, 8H); 3.0–3.4 (m, 5H); 6.01 (s, 1H); 6.8 (m, 2H); 7.05 (m, 2H); 7.35 (m, 5H).

EXAMPLE 23

(E)-3-[3-(4-Fluorophenyl)-1-hexahydroazepinyl-5-isopropyl-2-phenyl-pyrrol-4-yl]-prop-2-enal

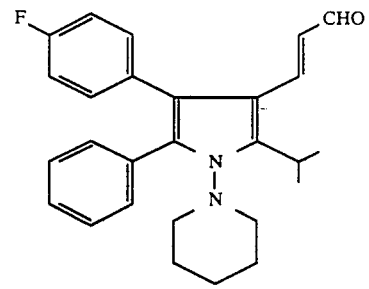

550 mg (1.5 mmol) of the compound from Example 22 are reacted analogously to Example 4.

Yield: 410 mg (63.6% of theory).

$^1$H-NMR (CDCl$_3$): δ=1.28–1.7 (m, 8H); 1.5 (d, 6H); 3.08 (m, 2H); 3.28 (m, 2H); 3.58 (m, 1H); 5.7 (dd, 1H); 6.84 (m, 2H); 7.02 (m, 2H); 7.21 (m, 5H); 7.6 (d, 1H); 9.35 (d, 1H).

EXAMPLE 24

Methyl (E)-7-[3-(4-fluorophenyl)-1-hexahydroazepinyl-5-isopropyl-2-phenyl-pyrrol-4-yl]-5-hydroxy-3-oxo-hept-6-enoate

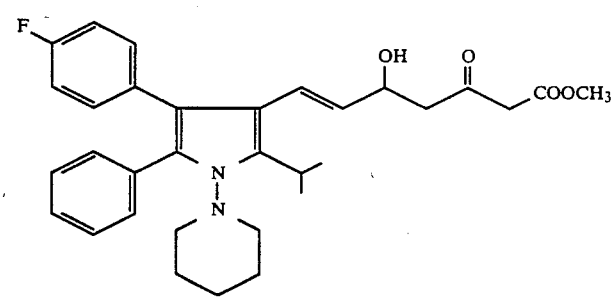

400 mg (0.93 mmol) of the compound from Example 23 are reacted analogously to Example 5.

Yield: 187 mg (36.8% of theory).

$^1$H-NMR (CDCl$_3$): δ=1.42 (d, 6H); 1.30–1.80 (m, 8H); 2.58 (m, 2H); 3.08 (m, 2H); 3.30 (m, 2H); 3.42 (m, 1H); 3.48 (s, 2H); 3.73 (s, 3H); 4.53 (m, 1H); 5.08 (dd, 1H); 6.68 (d, 1H); 6.82 (m, 2H); 7.04 (m, 2H); 7.22 (m, 5H).

EXAMPLE 25

Methyl erythro-(E)-7-[3-(4-fluorophenyl)-1-hexahydroazepinyl-5-isopropyl-2-phenyl-pyrrol-4-yl]-3,5-dihydroxyhept-6-enoate

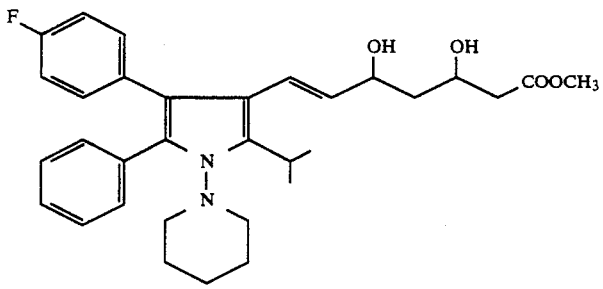

180 mg (0.33 mmol) of the compound from Example 24 are reacted analogously to Example 6.

Yield: 130 mg (72.2% of theory).

$^1$H-NMR (CDCl$_3$): δ=1.43 (d, 6H); 1.20–1.80 (m, 10H); 2.74 (m, 2H); 3.10 (m, 2H); 3.31 (m, 2H); 3.41 (m, 1H); 3.72 (s, 3H); 4.19 (m, 1H); 4.33 (m, 1H); 5.12 (dd, 1H); 6.62 (d, 1H); 6.80 (m, 2H); 7.03 (m, 2H); 7.22 (m, 5H).

EXAMPLE 26

3-(4-Fluorophenyl)-5-isopropyl-1-(4-methylpiperidino)-2-phenyl-pyrrole

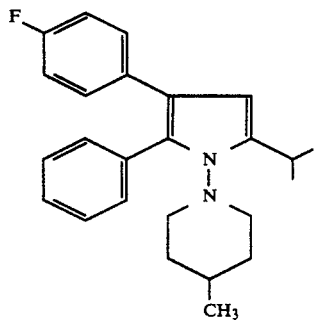

3.4 ml of conc. hydrochloric acid are added to 10.1 g (34 mmol) of the compound from Example 2 and 11.6 g (102 mmol) of N-amino-4-methyl-piperidine in 100 ml of toluene AR and 50 ml of dimethylformamide and the mixture is boiled for 24 hours in a water separator. The mixture is cooled, diluted using 200 ml of ethyl acetate and extracted three times using 1N hydrochloric acid and twice using saturated sodium hydrogen carbonate solution. The organic phase is dried over magnesium sulphate and concentrated in vacuo, and the residue is chromatographed on a column (silica gel 70–230 mesh, using ethyl acetate/petroleum ether 5:95).

Yield: 1.9 g (14.8% of theory).

EXAMPLE 27

E-(3)-[3-(4-Fluorophenyl)-5-isopropyl-1-(4-methylpiperidino)-2-phenyl-pyrrol-4-yl]-prop-2-enal

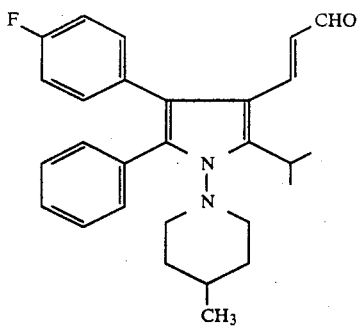

1.9 g (5.1 mmol) of the compound from Example 26 are reacted analogously to Example 4.

Yield: 1.2 g (54.5% of theory).

$^1$H-NMR (CDCl$_3$): δ=0.88 (d, 3H); 1.0–1.70 (m, 5H); 1.48 (d, 6H); 2.97 (m, 2H); 3.12 (m, 2H); 3.56 (m, 1H); 5.77 (dd, 1H); 6.82 (m, 2H); 7.0 (m, 2H); 7.27 (m, 5H); 7.52 (d, 1H); 9.38 (d, 1H).

EXAMPLE 28

Methyl (E)-7-[3-(4-fluorophenyl)-5-isopropyl-1-(4-methylpiperidino)-pyrrol-4-yl]-5-hydroxy-3-oxo-hept-6-enoate

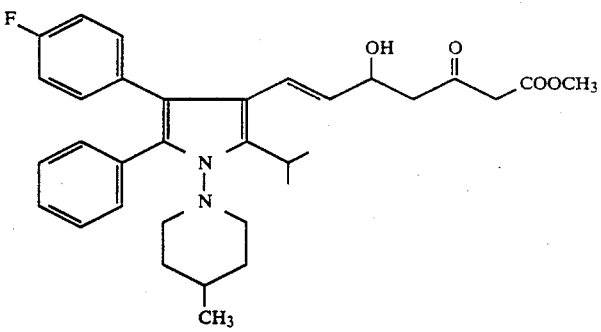

1.2 g (2.8 mmol) of the compound from Example 27 are reacted analogously to Example 5.

Yield: 850 mg (55.6% of theory).

$^1$H-NMR (CDCl$_3$): δ=0.87 (d, 3H); 1.0–1.70 (m, 5H); 1.42 (d, 6H); 2.62 (m, 2H); 2.91 (m, 2H); 3.09 (m, 2H) 3.40 (m, 1H); 3.48 (s, 2H); 3.73 (s, 3H); 4.55 (m, 1H); 5.18 (dd, 1H); 6.52 (d, 1H); 6.78 (m, 2H); 6.99 (m, 2H); 7.25 (m, 5H).

EXAMPLE 29

Methyl erythro-(E)-7-[3-(4-fluorophenyl)-5-isopropyl-1-(4-methylpiperidino)-pyrrol-4-yl]-3,5-dihydroxy-hept-6-enoate

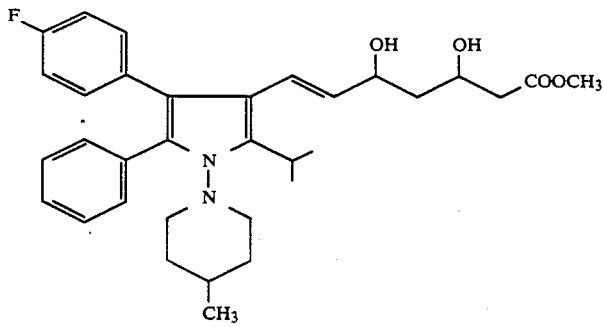

830 mg (1.7 mmol) of the compound from Example 28 are reacted analogously to Example 6.

Yield: 620 mg (66.5% of theory).

$^1$H-NMR (CDCl$_3$): δ=0.87 (d, 3H); 1.0–1.7 (m, 7H); 1.39 (d, 6H); 2.47 (m, 2H); 2.90 (m, 2H); 3.12 (m, 2H); 3.39 (m, 1H); 3.72 (s, 3H); 4.22 (m, 1H); 4.38 (m, 1H); 5.22 (dd, 1H); 6.48 (d, 1H); 6.76 (m, 2H); 6.98 (m, 2H); 7.25 (m, 5H).

Use Example

EXAMPLE 30

The determination of enzyme activity was carried out as modified by G. C. Ness et al., Archives of Biochemistry and Biophysics 197, 493–499 (1979). Male Rico rats (body weight 300–400 g) were treated for 11 days with Altromin powdered feed to which 40 g of cholestyramine/kg of feed had been added. After decapitation, the livers were removed from the animals and placed on ice. The livers were comminuted and homogenized 3 times in a Potter-Elvejem homogenizer in 3 volumes of 0.1 M saccharose, 0.05 M KCl, 0.04 M K$_x$H$_y$ phosphate, 0.03 M ethylenediaminetetraacetic acid, 0.002 M dithiothreitol (SPE) buffer pH 7.2. The mixture was subsequently centrifuged at 15,000* g for 15 minutes and the sediment was discarded. The supernatant was sedimented at 100,000 g for 75 minutes. The pellet is taken up in ¼ volume of SPE buffer, homogenized again and subsequently centrifuged again for 60 minutes at 100,000 g. The pellet is taken up using a 5-fold amount of its volume of SPE buffer, homogenized and frozen and stored at −78° C. (=enzyme solution).

For testing, the test compounds (or mevinolin as a reference substance) were dissolved in dimethylformamide with the addition of 5% by volume of 1N NaOH and employed in various concentrations in the enzyme test using 10 μl. The test was started after preincubation of the compounds with the enzyme at 37° C. for 20 minutes. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase, 35 μmol K$_x$H$_y$ phosphate pH 7.2, 20 μl of enzyme preparation and 56 nmol of 3-hydroxy-3-methyl-glutaryl coenzyme A (glutaryl-3-$^{14}$C) 100,000 dpm.

The test batch was incubated for 60 minutes at 37° C. and the reaction was stopped by addition of 300 μl of 0.24 M HCl. After a post-incubation of 60 minutes at 37° C., the batch was centrifuged and 600 μl of the supernatant were applied to a 0.7×4 cm column packed with Biorex ® 5-chloride 100–200 mesh (anion exchanger). The column was subsequently washed with 2 ml of distilled water and 3 ml of aquasol were added to runnings plus washing water and counted in an LKB scintillation counter. IC$_{50}$ values were determined by intrapolation by plotting the percentage inhibition against the concentration of the compound in the test. To determine the relative inhibitory potency, the IC$_{50}$ value of the reference substance mevinolin was set as 100 and compared with the simultaneously determined IC$_{50}$ value of the test compound.

EXAMPLE 31

The subchronic action of the compounds according to the invention on the blood cholesterol levels in dogs was tested in feeding experiments lasting several weeks. To this end, the substance to be investigated was administered p.o. together with the feed once daily in a capsule to healthy beagle hounds over a period of several weeks. In addition, the feed was admixed over the entire experimental period, i.e. before, during and after the period of administration of the substance to be investigated, with colestyramine (4 g/100 g of feed) as a biol acid sequesterent. Venous blood was taken from the dogs twice weekly and the serum cholesterol was determined enzymatically. The serum cholesterol levels during the period of administration were compared with the serum cholesterol levels before the period of administration (control).

It will be appreciated that the instant specification and claims are set forth by way of illustration and not limitation, and that various modifications and changes may be made without departing from the spirit and scope of the present invention.

What is claimed is:

1. An N-substituted N-amino-pyrrole of the formula

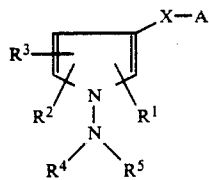

wherein

R¹ stands for cyclopropyl, cyclopentyl or cyclohexyl, or
  stands for lower alkyl which can be substituted by fluorine, chlorine, bromine, cyano, hydroxyl, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, by a group of the formula NR⁶R⁷, wherein
    R⁶ and R⁷ are identical or different and denote lower alkyl, phenyl, benzyl, acetyl, benzoyl, phenylsulphonyl or lower alkylsulphonyl,
  benzyloxy, benzylthio, benzylsulphonyl, phenylethoxy, phenylethylthio or phenylethylsulphonyl, where the aryl radicals mentioned can be monosubstituted or disubstituted by identical or different fluorine, chlorine, bromine, lower alkyl, lower alkoxy, trifluoromethyl or trifluoromethoxy, R² stands for phenyl or naphthyl, each of which can be monosubstituted to tetrasubstituted by identical or different lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —NR⁶R⁷, R³ stands for hydrogen or
  for cyclopropyl, cyclopentyl or cyclohexyl or
  for lower alkyl which can be substituted by fluorine, chlorine, cyano, hydroxyl, lower alkoxy, lower alkylthio, lower alkylsulphonyl, trifluoromethyl, lower alkoxycarbonyl, benzoyl or lower alkylcarbonyl, or by a group of the formula —NR⁶R⁷,
  or phenyl, phenoxy, phenylsulphonyl, benzyloxy or phenylethoxy, where the aryl radicals mentioned can be monosubstituted or disubstituted by identical or different fluorine, chlorine, lower alkyl, lower alkoxy or trifluoromethyl,
  or
  denotes phenyl or naphthyl, which can be monosubstituted or disubstituted by identical or different lower alkyl, lower hydroxyalkyl, lower alkoxy, phenyl, phenyloxy, benzyl, benzyloxy, phenethyl, phenylethoxy, fluorine, chlorine, cyano, trifluoromethyl or lower alkoxycarbonyl, or by a group of the formula —NR⁶R⁷, R⁴ and R⁵ can be identical or different and
  stand for hydrogen,
  stand for cyclopropyl, cyclopentyl or cyclohexyl,
  or stand for lower alkyl which can be substituted by fluorine, chlorine, hydroxyl, lower alkoxy, trifluoromethyl or benzoyl, or by a group of the formula —NR⁶R⁷,
  or phenyl, phenoxy, benzyloxy or phenylethoxy, where the aryl radicals mentioned can be monosubstituted or disubstituted by identical or different fluorine, chlorine, lower alkyl, lower alkoxy or trifluoromethyl, or
  stand for phenyl or naphthyl, each of which can be monosubstituted or disubstituted by identical or different lower alkyl, lower alkoxy, lower alkylthio, lower alkylsulphonyl, phenyl, phenyloxy, phenylthio, phenylsulphonyl, benzyl, benzyloxy, phenethyl, phenylethoxy, fluorine, chlorine, cyano, trifluoromethyl or lower alkoxycarbonyl, or by a group of the formula —NR⁶R⁷,
  or R⁴ and R⁵, together with the N atom, form a 5- to 7-membered heterocycle which can be substituted by lower alkyl, X stands for a group of the formula —CH₂—CH₂— or —CH=CH—, and A stands for a group of the formula

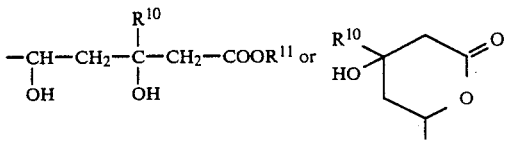

wherein

R¹⁰ denotes hydrogen or lower alkyl, and
R¹¹ denotes a C₁-C₆-alkyl radical, a C₆-C₁₂-alkyl radical or a C₇-C₁₀-alkyl radical or
  denotes a physiologically tolerable cation.

2. A substituted N-amino-pyrrole according to claim 1, wherein

R¹ stands for cyclopropyl, cyclopentyl or cyclohexyl, or
  stands for methyl, ethyl, propyl, isopropyl, butyl, sec.-butyl or tert.butyl, each of which can be substituted by fluorine, chlorine, hydroxyl, methoxy, ethoxy, propoxy, isopropoxy, butoxy, sec. butoxy, tert.butoxy, methylthio, ethylthio, propylthio, isopropylthio, methylsulphonyl, ethylsulphonyl, propylsulphonyl, isopropylsulphonyl, trifluoromethyl, methoxycarbonyl, ethoxycarbonyl, butoxycarbonyl, isobutoxycarbonyl, tert.-butoxycarbonyl, benzoyl, acetyl, phenyl, phenoxy, phenylsulphonyl, benzyloxy, benzylthio or benzylsulphonyl, R² stands for phenyl which can be monosubstituted or disubstituted by identical or different methyl, ethyl, propyl, isopropyl, butyl, isobutyl, tert.-butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, methoxycarbonyl, ethoxycarbonyl, propoxycarbonyl, isopropoxycarbonyl, butoxycarbonyl, isobutoxycarbonyl or tert.butoxycarbonyl, R³ denotes hydrogen, cyclopropyl, cyclopentyl or cyclohexyl, or
  denotes methyl, ethyl, propyl, isopropyl, butyl, isobutyl, tert.butyl, pentyl, isopentyl, hexyl or isohexyl, which can be substituted by fluorine, chlorine, cyano, hydroxyl, methoxy, ethoxy, propoxy, isopropoxy, butoxy, isobutoxy, tert.butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, trifluoromethyl, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group —$NR^6R^7$, where
  $R^6$ and $R^7$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, $R^4$ and $R^5$ can be identical or different and
  stand for hydrogen, cyclopropyl, cyclopentyl or cyclohexyl, or
  stand for methyl, ethyl, propyl, isopropyl, butyl, isobutyl, tert.butyl, pentyl, isopentyl, hexyl or isohexyl, each of which can be substituted by fluorine, chlorine, hydroxyl, methoxy, ethoxy, methylthio, ethylthio, propylthio, isopropylthio, butylthio, isobutylthio, tert.butylthio, benzoyl, acetyl or ethylcarbonyl, or by a group —$NR^6R^7$, or by phenyl, phenoxy, phenylthio, phenylsulphonyl and benzyloxy, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.-butoxy or trifluoromethyl, or
  stand for phenyl which can be monosubstituted or disubstituted by identical or different methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.-butoxy, methylthio, ethylthio, propylthio, isopropylthio, butylthio, isobutylthio, tert.butylthio, methylsulphonyl, phenyl, phenoxy, phenylthio, phenylsulphonyl, benzyl, benzyloxy, fluorine, chlorine, cyano, hydroxyl, trifluoromethyl, methoxycarbonyl, ethoxycarbonyl, propoxycarbonyl, isopropoxycarbonyl, butoxycarbonyl, isobutoxycarbonyl or tert.butoxycarbonyl, or by a group —$NR^6R^7$,
  or
$R^4$ and $R^5$, together with the N atom, form a 5- to 7-membered heterocycle which can be substituted by lower alkyl,
X stands for a group of the formula —$CH_2$—$CH_2$— or —$CH=CH$—, and
A stands for a group of the formula —CH—CH$_2$—C—CH$_2$—COOR$^{11}$ or (with $R^{10}$ substituents, OH groups) or cyclic lactone structure with $R^{10}$, HO wherein
$R^{10}$ denotes hydrogen, and
$R^{11}$ denotes hydrogen, methyl, ethyl, propyl, isopropyl, butyl, isobutyl, tert.butyl or benzyl or denotes a sodium, potassium, calcium or magnesium or ammonium ion.

3. An N-substituted N-amino-pyrrole according to claim 1, wherein
$R^1$ stands for cyclopropyl, methyl, ethyl, propyl, isopropyl, butyl, isobutyl or tert.-butyl, each of which can be substituted by fluorine, chlorine, hydroxyl, methoxy, phenyl or phenoxy, $R^2$ stands for phenyl which can be monosubstituted or disubstituted by identical or different methyl, ethyl, propyl, isopropyl, butyl, isobutyl, tert.-butyl, hydroxymethyl, methoxy, ethoxy, propoxy, phenoxy, benzyloxy, fluorine, chlorine, cyano or trifluoromethyl, $R^3$ stands for hydrogen,
  stands for cyclopropyl,
  stands for methyl, ethyl, propyl or isopropyl, each of which can be substituted by fluorine, hydroxyl, chlorine, cyano or trifluoromethyl,
  stands for phenyl which can be substituted by fluorine, chlorine, cyano, hydroxyl or trifluoromethyl, $R^4$ and $R^5$ are identical or different and
  stand for methyl, ethyl, propyl, isopropyl, butyl or tert.-butyl, or
  stand for phenyl which can be monosubstituted or disubstituted by identical or different methyl, ethyl, propyl, isopropyl, methoxy, fluorine, chlorine, hydroxyl, trifluoromethyl or methoxycarbonyl, or
$R^4$ and $R^5$, together with the N atom, form a 5- to 7-membered heterocycle, which can be substituted by lower alkyl,
X stands for a group of the formula ∕∕∕∕ (E-configuration)

and
A stands for a group of the formula

—CH—CH$_2$—C—CH$_2$—COOR$^{11}$ or (R$^{10}$, HO structure with cyclic lactone)

wherein
$R^{10}$ denotes hydrogen and
$R^{11}$ denotes hydrogen, methyl or ethyl or denotes a sodium or potassium cation.

4. An N-substituted N-amino-pyrrole according to claim 1, of the formula (Ia) and (Ib) pyrrole structures with substituents $R^1$, $R^2$, $R^3$, $R^4$, $R^5$, X—A in which
$R^1$ stands for cyclopropyl, or lower alkyl,
$R^2$ stands for phenyl which can be monosubstituted or disubstituted by identical or different hydroxymethyl, phenoxy, benzyloxy or fluorine,
$R^3$ stands for hydrogen, cyclopropyl, lower alkyl, or phenyl which can be substituted by fluorine or hydroxyl,
$R^4$ and $R^5$ are identical or different and stand for lower alkyl or phenyl,
or R[4] and R[5] together with the N-atom form a 5- to 7-membered heterocycle, which can be substituted by lower alkyl, X stands for a group of the formula

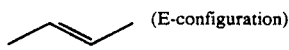

(E-configuration)

and

A stands for a group of the formula

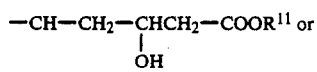

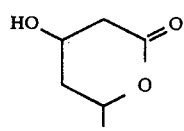

wherein

R[11] denotes hydrogen, lower alkyl or a sodium or potassium cation.

5. A compound according to claim 1, wherein such compound is methyl 7-[3-(4-fluorophenyl)-5-isopropyl-2-phenyl-1-(1-pyrrolidinyl)-pyrrol-4-yl]-3,5-dihydroxy-hept-6-enoate of the formula

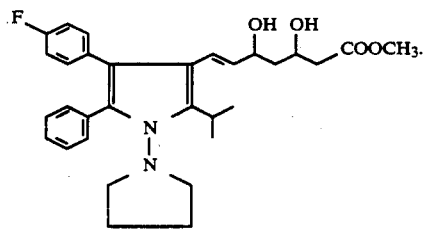

6. A compound according to claim 1, wherein such compound is methyl 7-[3-(4-fluorophenyl)-5-isopropyl-2-phenyl-1-piperidino-pyrrol-4-yl]-3,5-dihydroxy-hept-6-enoate of the formula

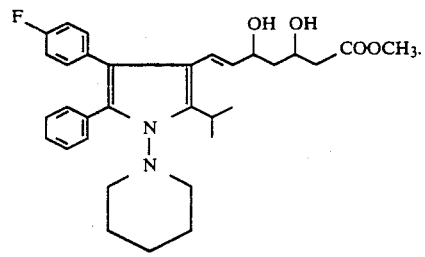

7. A compound according to claim 1, wherein such compound is methyl 7-[3-(4-fluoro-3-phenoxyphenyl)-5-isopropyl-2-methyl-1-piperidino-pyrrol-4-yl]-3,5-dihydroxy-hept-5-enoate of the formula

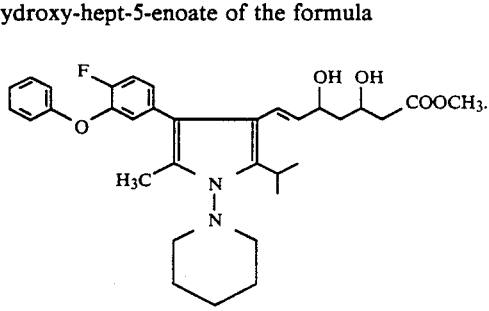

8. An HMG-CoA reductase-inhibiting composition comprising an amount effective therefor of a compound according to claim 1 and a diluent.

9. A composition according to claim 8 in the form of a tablet, capsule or ampule.

10. A method of inhibiting HMG-CoA reductase in a patient in need thereof which comprises administering to such patient an amount effective therefor of a compound according to claim 1.

11. The method according to claim 10, wherein such compound is

7-[3-(4-fluorophenyl)-5-isopropyl-2-phenyl-1-(1-pyrrolidinyl)-pyrrol-4-yl]-3,5-dihydroxy-hept-6-enoate, 7-[3-(4-fluorophenyl)-5-isopropyl-2-phenyl-1-piperidino-pyrrol-4-yl]-3,5-dihydroxy-hept-6-enoate, or 7-[3-(4-fluoro-3-phenoxyphenyl)-5-isopropyl-2-methyl-1-piperidino-pyrrol-4-yl]-3,5-dihydroxy-hept-5-enoate.

* * * * *